United States Patent
Ramesh et al.

(10) Patent No.: US 10,542,889 B2
(45) Date of Patent: Jan. 28, 2020

(54) SYSTEMS, METHODS, AND DEVICES FOR REMOTE HEALTH MONITORING AND MANAGEMENT

(71) Applicant: AMRITA VISHWA VIDYAPEETHAM, Kollam (IN)

(72) Inventors: Maneesha Vinodini Ramesh, Kollam (IN); Rahul Krishnan Pathinarupothi, Palakkad (IN); Ekanath Srihari Rangan, Coimbatore (IN)

(73) Assignee: AMRITA VISHWA VIDYAPEETHAM, Kollam (IN)

( * ) Notice: Subject to any disclaimer, the term of this patent is extended or adjusted under 35 U.S.C. 154(b) by 0 days.

(21) Appl. No.: 16/103,159

(22) Filed: Aug. 14, 2018

(65) Prior Publication Data

US 2019/0046039 A1 Feb. 14, 2019

(30) Foreign Application Priority Data

Aug. 14, 2017 (IN) .............................. 201741028828

(51) Int. Cl.
    - G08B 23/00 (2006.01)
    - G08C 15/06 (2006.01)
    - A61B 5/00 (2006.01)
    - G16H 80/00 (2018.01)
    - A61B 5/145 (2006.01)
    - G16H 10/60 (2018.01)

(52) U.S. Cl.
    CPC .......... *A61B 5/0024* (2013.01); *G16H 80/00* (2018.01); *A61B 5/0006* (2013.01); *A61B 5/0022* (2013.01); *A61B 5/0031* (2013.01); *A61B 5/14532* (2013.01); *A61B 5/7275* (2013.01); *G16H 10/60* (2018.01)

(58) Field of Classification Search
    CPC ... A61B 5/0024; A61B 5/0006; A61B 5/0031; A61B 5/14532; A61B 5/0022; A61B 5/7275; G16H 80/00; G16H 10/60
    USPC ...................................................... 340/870.02
    See application file for complete search history.

(56) References Cited

U.S. PATENT DOCUMENTS 7,978,062 B2  7/2011  Lalonde et al.
9,186,077 B2  11/2015 Ma et al.
(Continued)

*Primary Examiner* — Tanmay K Shah
(74) *Attorney, Agent, or Firm* — Convergence Intellectual Property Law P.C.; Jonathan Garfinkel

(57) ABSTRACT

A remote health monitoring system, method and device is disclosed. The systems utilize one or more sensors, data aggregation and transmission units, mobile computing devices, processing, analytics and storage (PAS) units, and a framework based on a novel location- and power-aware communication systems and analytics to notify and manage patient health. Methods to transmit data to a PAS unit through the patients' smart phone that is connected to internet, abnormality detection in the data, advanced analytical diagnostics and communication system between the health service provider (HSP) and patient are also provided. The health monitoring systems, methods and devices allows for continuous monitoring of the patient without disrupting their normal lives, provides access even in sparsely connected and remote regions which lack good healthcare facilities, allows intervention by specialized practitioners, and sharing of resource or information in the existing healthcare facilities.

26 Claims, 16 Drawing Sheets

(56) References Cited

U.S. PATENT DOCUMENTS

| | | | |
|---|---|---|---|
| 2013/0181832 A1* | 7/2013 | Landau | G08B 21/02 |
| | | | 340/539.12 |
| 2014/0136223 A1* | 5/2014 | Phillips | G06Q 10/10 |
| | | | 705/2 |
| 2015/0066538 A1 | 3/2015 | Dantsker et al. | |
| 2017/0181645 A1* | 6/2017 | Mahalingam | A61B 5/0004 |
| 2017/0300654 A1* | 10/2017 | Stein | A61B 5/0022 |
| 2018/0144100 A1* | 5/2018 | Chalas | G08B 25/08 |
| 2018/0296143 A1* | 10/2018 | Anderson, III | A61B 5/14532 |
| 2019/0019578 A1* | 1/2019 | Vaccaro | G16H 20/30 |

\* cited by examiner

| Power Management Factors | | Battery Level | | |
|---|---|---|---|---|
| Location | Priority | Low | Medium | High |
| In-ward Telemetry | Routine | Delayed | Immediate | Immediate |
| | Critical | Immediate | Immediate | Immediate |
| Outdoor | Routine | Delayed | Delayed | Local PAS + Delayed |
| | Critical | Immediate | Immediate | Local PAS + Immediate |
| Indoor | Routine | Local PAS + Delayed | Local PAS + Immediate | Local PAS + Immediate |
| | Critical | Immediate | Immediate | Local PAS + Immediate |

FIG. 5D

SYSTEMS, METHODS, AND DEVICES FOR REMOTE HEALTH MONITORING AND MANAGEMENT

CROSS-REFERENCES TO RELATED APPLICATIONS

The present application claims priority to Indian Patent Application No. 201741028828, filed on Aug. 14, 2017, which is incorporated herein by reference in its entirety.

FIELD OF THE INVENTION

The invention generally relates to body sensor tracking and monitoring platforms, and in particular, to health monitoring systems, methods, and devices to remotely monitor and track patient health status.

DESCRIPTION OF RELATED ART

Present healthcare technologies allow for body sensors or implants attached to a patient to be used in medical monitoring and detection of emergency conditions in at-risk patients. However, the patient usually has to present himself at a local healthcare facility for accurate measurements, gain access to Hospital Information Systems (HIS) and advanced analytics, and subsequently wait for the assessment of the data by the Health Service Provider (HSP). Remote monitoring of the patient is greatly desired in such patients as it allows for continuous monitoring of the patient without disrupting their normal lives, provides access from remote areas that lack good healthcare facilities, allows intervention by specialized practitioners, and sharing of resource or information in the existing healthcare facilities.

Various publications have attempted to remote healthcare services. For example, U.S. Pat. No. 7,978,062B2 discloses medical data transport over wireless life critical network. US20150066538A1 discloses a communication device resource allocation based on medical data criticality and resource status. U.S. Pat. No. 9,186,077B2 discloses method and devices with customizable power management providing wireless communication of heart rate data of users. Although systems for managing medical conditions have been described, they are largely limited to urban areas with good infrastructure and connectivity. There remains a need to provide monitoring methods and systems from remote areas that are sparsely connected.

Furthermore, there remains a need for access to relevant medical information, processing, analytics and communication for timely intervention of an adverse event occurring in patients located in remote areas while excluding minor aberrational data that may not be indicative of any serious condition.

SUMMARY OF THE INVENTION

The present subject matter, in general, relates to body sensor tracking and monitoring platforms, and in particular, to remote health monitoring system, method and device to remotely monitor and track patient health status.

The invention in various embodiments includes a method for remote monitoring of a patient that includes the steps of obtaining a sensor data from one or more sensors attached to the patient's body, transmitting the sensor data to a first mobile computing device. The sensor data from the sensors is transmitted to the mobile computing device through a wired or a short range wireless communication network. The sensor data is transmitted to a processing, analytics and storage (PAS) unit, wherein the first mobile computing device transmits the data to the PAS unit through a wireless communication network. In some embodiments one or more abnormalities are detected and determined in the sensor data by periodic assessment of the sensor data in the first mobile computing device, the PAS unit or a combination thereof. A quantized severity for the one or more abnormalities in the PAS unit is determined wherein said determining comprise converting raw sensor values to a series of clinically relevant severity symbols. In some embodiments the one or more abnormality that exceed a severity threshold for the patient is identified from one or more abnormality to exceed a personalized severity threshold over the assessment period, wherein the severity threshold for the patient is determined from sensor data, inter-sensor correlation, patient's historical data, doctor's inputs, inter-patient machine learning models obtained from hospital information system (HIS), or a combination thereof. Further a notification of the one or more abnormality is sent to the first mobile computing device and to a second mobile computing device, wherein the second mobile computing device is connected to a Health Service Provider (HSP) and said notification includes an estimate of time available to the HSP for effective intervention. Furthermore, the HSP can choose to selectively obtain more precise data from the first mobile computing device or from the PAS unit based on a technique called Detailed Data-on-Demand (DD-on-D).

In some embodiments the sensor data is obtained from one or more sensors attached to the patient's body that includes obtaining blood pressure level, blood glucose level, oxygen saturation (SpO2) level, electrocardiogram (ECG) data, motion detection system data, accelerometer data, GPRS data, or a combination thereof. In some embodiments detecting the one or more abnormality in sensor data is indicative of a cardiovascular disease in the patient.

In some embodiments transmitting the sensor data to the first mobile computing device includes transmitting over a GSM, 2G, 3G, 4G, LTE, Wi-Fi network or an Ad-hoc network created with neighboring wireless terminals. Further the sensor data is transmitted to one or more mobile computing device connected to other patients or HSP over a wireless network.

In some embodiments the sensor data is transmitted to a processing, analytics and storage (PAS) unit includes transmitting to a local PAS unit, a remote PAS unit, a hospital PAS unit comprising a hospital information system (HIS), or a combination thereof.

In various embodiments a notification of the abnormality is send to a second mobile computing device that includes presenting patient health status to health service provider based on the criticality of data. In some embodiments the sensor data is analyzed by visualization, monitoring, analysis or intervention tools by the health service provider.

In some embodiments the method includes directing the abnormality to a doctor, hospital, caregiver, or emergency responder to attend to the patient. In some embodiments the medium of notification of the second mobile computing device is determined based on data criticality, patient profile, available communication media, power availability of the mobile computing devices and sensors, location of the at least one processing, analytics and storage (PAS) unit, or a combination thereof. In some embodiments the method includes pulling a sensor data from the first mobile device that uses a SMS sent from the second mobile device to the first mobile device. In some embodiments, method includes sending a request for data from the second mobile device to the first mobile computing device and obtaining the data from the first mobile device, the PAS unit, or a combination thereof in an increasing order of precision, starting from just alerts, then getting severity quantization levels, or frequency maps of how many time the severity thresholds are crossed, and then the raw sensor data. In some embodiments, the data is obtained from a request sent from the second mobile device to the first mobile device as a SMS.

In various embodiments the severity is determined through a severity quantization technique that converts multi-sensor values to severity symbols based on a combination of sensor values, inter-sensor correlation, patient's historical data, doctors' inputs, and inter-patient machine learning model. In some embodiments the severity quantizer is adjusted such that the various sensor values are interpreted differently according to the diagnostic interest of one or more doctors. In various embodiments severity is quantized by using a data summarization and a detection algorithm for patient data severity that interprets a large amount of multi-sensor data. In some embodiments the method includes defining the routing and power policies based on reliable delivery of relevant health data to the HSPs.

In various embodiments the method further includes classifying the data as routine or critical data, sending the critical data via a higher priority channel such as a direct link or a cellular GSM and sending routine data using any available channel. In various embodiments the communication from the PAS unit is prioritized based on a combination of user location using GPS or other localization techniques, power availability in the mobility of data via smartphone and sensors, and health criticality of the patient.

In various embodiments the invention is a system for use in remote monitoring of a patient, that includes at least one sensor attached to the patient's body to obtain sensor data, a data aggregation and transmission unit, wherein the data aggregation and transmission unit is interfaced with the at least one sensor to receive the sensor data, a first mobile computing device, wherein the first mobile computing device is configured to receive and transmit the sensor data through a wireless communication network, at least one processing, analytics and storage (PAS) unit, wherein the PAS unit is configured to receive the sensor data from the first mobile computing device, wherein the first mobile computing device, the PAS unit, or a combination thereof is configured to detect one or more abnormality in the sensor data, quantize a severity and identify if quantized severity exceeds a personalized severity threshold over the assessment period for the patient based on sensor data, inter-sensor correlation, patient's historical data, doctor's inputs, inter-patient machine learning models obtained from hospital information system (HIS), or a combination thereof and a second mobile computing device, wherein the second mobile computing device is connected to a Health Service Provider (HSP), wherein the system is configured to notify the first and the second mobile computing devices when the quantized severity exceeds the severity threshold and includes an estimate of time available to the HSP for effective intervention.

In various embodiments the system that includes at least one sensor is a BP sensor, a glucose sensor, a SpO2 sensor, an ECG sensor, a motion detection system, an accelerometer, a GPRS, or a combination thereof.

In various embodiments the first mobile computing device, the second mobile computing device, or both is a smartphone, handheld, tablet, laptop, or a wearable device. In some embodiments the first mobile computing device is configured to transmit the sensor data through a GSM, 2G, 3G, 4G, LTE, Wi-Fi network or an Ad-hoc network created with neighboring wireless terminals. In various embodiments' the at least one PAS unit comprises a local server, a remote server or a hospital server that are connected by a wireless network.

In some embodiments the hospital server comprises a hospital information management system (HIM). In various embodiments the PAS unit includes an Application Layer with various visualization, monitoring, analysis and intervention tools. In various embodiments the medium of notification for the first and second mobile computing device is determined based on data criticality, patient profile, available communication media, power availability of the mobile computing devices and sensors, location of the at least one processing, analytics and storage (PAS) unit, or a combination thereof.

A computer program product having non-volatile memory therein, carrying computer executable instructions stored thereon for remote monitoring of a patient. The instructions include obtaining a sensor data from one or more sensors attached to the patient's body. The instructions next include transmitting the sensor data to a first mobile computing device, wherein the sensor data is transmitted to the mobile computing device through a wired or a short range wireless communication network. Further, the instructions cause transmitting the sensor data to a processing, analytics and storage (PAS) unit, wherein the first mobile computing device transmits the data to the PAS unit through a wireless communication network. The instructions further include detecting one or more abnormalities in the sensor data, wherein said one or more abnormalities is determined by periodic assessment of the sensor data in the first mobile computing device, the PAS unit or a combination thereof. Next, the instructions involve determining a quantized severity for the one or more abnormalities in the PAS unit, wherein said determining comprise converting raw sensor values to a series of clinically relevant severity symbols. The instructions then cause identifying the one or more abnormality to exceed a personalized severity threshold over the assessment period, wherein the severity threshold for the patient is determined from sensor data, inter-sensor correlation, patient's historical data, doctor's inputs, inter-patient machine learning models obtained from hospital information system (HIS), or a combination thereof. Further, the instructions include sending a notification of the one or more abnormality to the first mobile computing device. Finally, the instructions include sending a notification of the one or more abnormality to a second mobile computing device, wherein the second mobile computing device is connected to a Health Service Provider (HSP) and said notification includes an estimate of time available to the HSP for effective intervention.

This and other aspects are disclosed herein.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 5D illustrates a power management mechanism based on patient location and data priority.

DETAILED DESCRIPTION OF THE EMBODIMENTS

Figure 1A:
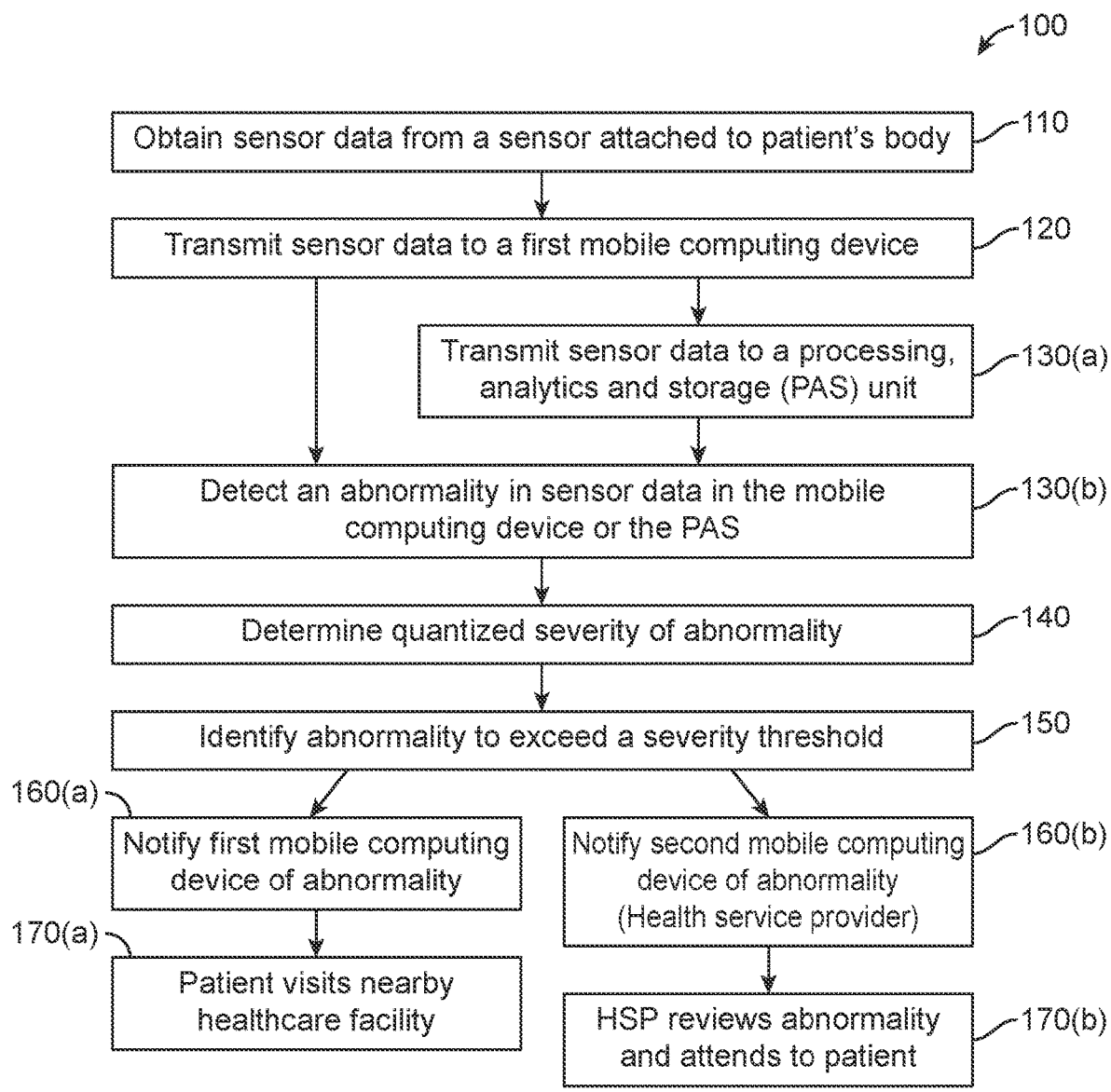
FIG. 1A shows a method for remote health monitoring of patients.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The present disclosure describes systems, methods, devices, and kits for remote monitoring and tracking of patient health status using one or more sensors, location- and power-aware communication systems and analytics. In one embodiment, a system for use in remote monitoring of a patient is provided. In another embodiment, the invention relates to a method of remote monitoring and tracking of patient health status even in sparsely connected and remote regions. In various embodiments the invention discloses system of rapid summarization for effective prognosis in wireless remote health monitoring (RASPRO). In yet other embodiments, a computer program product for remote monitoring of a patient is provided.

A method 100 for remote monitoring of a patient is provided herein, as illustrated in FIG. 1A. The method includes obtaining sensor data from one or more sensors attached to a patient's body in block 110. In block 120, the data is aggregated by a data aggregation and transmission unit and transmitted to a first mobile computing device through a wired or a short range wireless communication network. The next step may involve transmitting the sensor data to a processing, analytics and storage (PAS) unit through a wireless communication network in block 130($a$). One or more abnormalities may be detected in the sensor data by periodic assessment of the sensor data in block 130($b$). The processing may be either carried out in the first mobile computing device, or the PAS unit. In some embodiments, the method 100 further includes determining a quantized severity for the one or more abnormalities detected in block 140. The method includes identifying that the severity of the one or more abnormalities exceeds a severity threshold for the patient, in block 150. The severity threshold for the patient in some embodiments may be a set of predetermined values derived from sensor data, inter-sensor correlation, patient's historical data, doctor's inputs, inter-patient machine learning models, or a combination thereof. The next step 160($a$) or 160($b$) involves sending a notification of the one or more abnormalities to the first mobile computing device and the second mobile computing device associated with the Health Service Provider (HSP). In some embodiments sending a notification of the abnormality to the second mobile computing device includes presenting patient health status to health service provider based on the criticality of data. In some embodiments, the method may further include analyzing the sensor data by visualization, monitoring, analysis or intervention tools by the health service provider. The notification may also include an estimate of time available to the HSP for effective intervention. In one embodiment, the method may additionally include directing a doctor, hospital, caregiver, or emergency responder to attend to the patient, in block step 170($b$). In one embodiment, the medium of notification of the second mobile computing device in block 160($b$) is determined based on data criticality, patient profile, available communication media, power availability of the mobile computing devices and sensors, location of the at least one processing, analytics and storage (PAS) unit, or a combination thereof. In an alternate embodiment, in block 170($a$), the patient may visit a nearby healthcare facility to obtain medical attention.

In some embodiments, block 110 of the method 100 includes obtaining a sensor signal such as blood pressure level, a blood glucose level, an oxygen saturation (SpO2) level, an electrocardiogram (ECG) data, motion detection system data, accelerometer data, GPS data, or a combination thereof. In some embodiments, detecting the one or more abnormality in sensor data in block 130(*b*) involves detecting an abnormality that is indicative of a cardiovascular disease in the patient. In various embodiments, transmitting the sensor data to the first mobile computing device in step 120 includes transmitting over a GSM, 2G, 3G, 4G, LTE, Wi-Fi network or an Ad-hoc network created with neighboring wireless terminals. In one embodiment block 120 may additionally include transmitting the sensor data to one or more mobile computing devices or to HSP device over a wireless network. In various embodiments, transmitting the sensor data to the processing, analytics and storage (PAS) unit in block 130(*a*) includes transmitting to a local PAS unit, a remote PAS unit, a hospital PAS unit including a hospital information system (HIS), or a combination thereof.

Figure 1B:
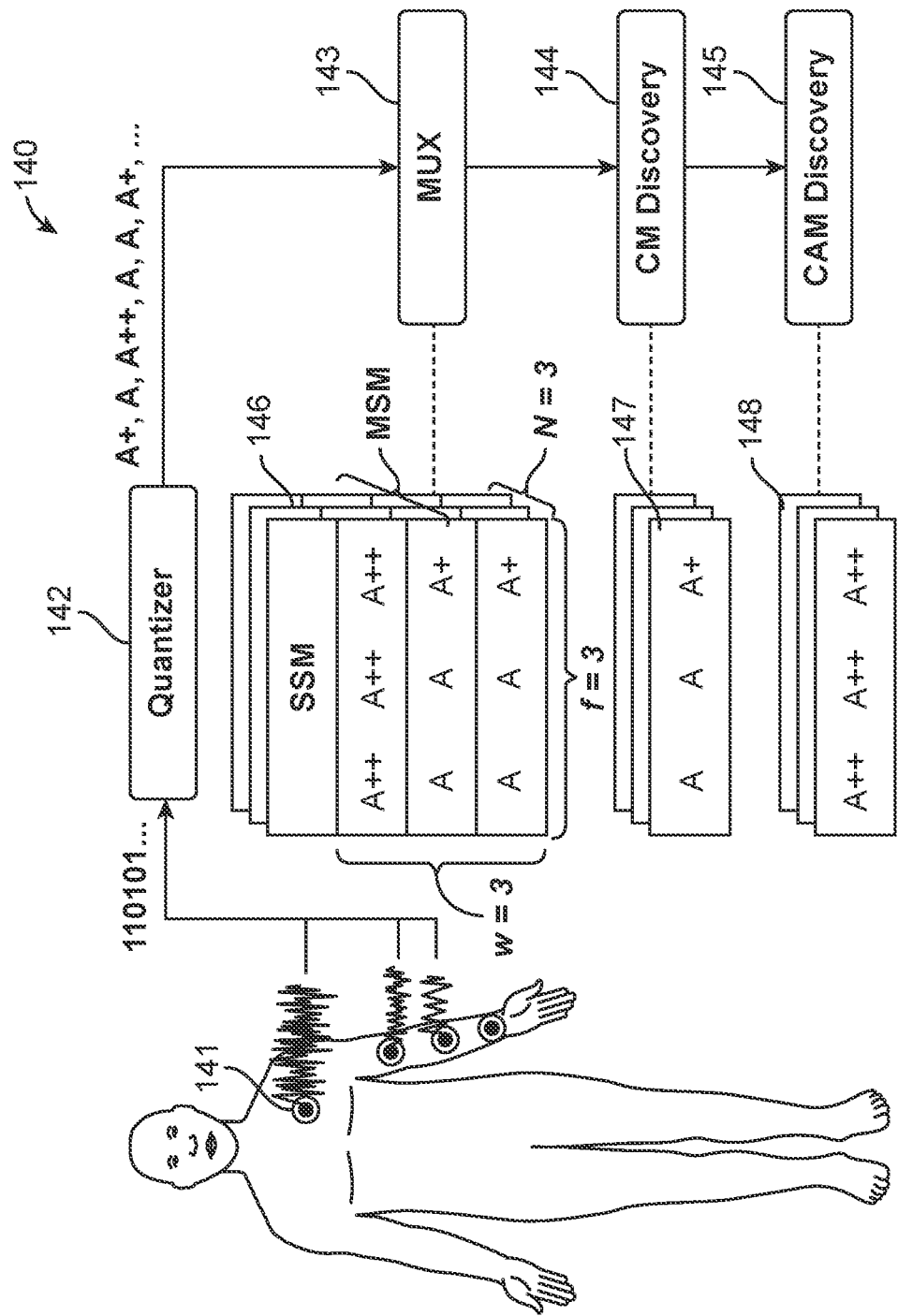
FIG. 1B shows a severity quantization technique that converts multi-sensor values to severity symbols.

In some embodiments, step 140 of method 100 includes determining severity through a severity quantization technique, as shown in FIG. 1B. The multi-sensor values obtained from the patient in 141 are converted to severity symbols based on a combination of sensor values, inter-sensor correlation, patient's historical data, doctors' inputs, inter-patient machine learning models among other factors. In various embodiments, the severity quantization includes sending the data to a data summarization and a detection module for patient data severity in 142. The module interprets a large amount of multi-sensor data and converts it to form sequence of severity symbols, called motifs that are arranged in a patient specific matrix as shown in FIG. 1B. In some embodiments, the module passes the quantized time series data to the MUX (multiplexer) in 143 as shown in FIG. 1B. In some embodiments, the MUX (multiplexer) arranges the quantized time series data into a three dimensional multi-sensor matrix (MSM) consisting of multiple 2-dimensional single sensor matrices (SSM). In an SSM 146, the quantized values, say A*t, A*t+1, A*t+2 etc. (where "*" represents severity values "+" or "++" or "−" or "−−", etc.), are arranged as increasing time series data in f columns and w rows, where f is the frequency of sensing and w is the observation window. Two different motifs are derived from any amount of large multi-sensor data (a) the most frequently occurring near normal trend in patients' data, called consensus normal motif (CM) as derived in 144, and (b) the most frequently occurring severe abnormality in the patient's data, called consensus abnormality motif (CAM) as derived in 145. In some embodiments, the method of identifying the motif is as illustrated in FIG. 1B, which compares individual data points in one sequence with other non-overlapping data points. In some embodiments, the comparison of individual data points is simplified as a quantized value A*t is compared with another value A*n, where n is a multiple of a constant time separation that is called comparison interval, denoted as I.

In one embodiment, the method is configured to generate clinically relevant alerts based on an aggregate criticality score called the "Alert Measure Index" (AMI) that is calculated using available time for doctor's intervention.

In some embodiments the continuous values from the sensors are converted to K different discrete severity level symbols for differentiating the quantized values from actual real values of the sensor data. In some embodiments, the normal values are assigned the symbol A, while above-normal and subnormal values are quantized into A++, A+, A−, A−−, etc., respectively, according to varying severity levels. The + symbol representing the above normal and − symbol representing subnormal values. In some embodiments, it is assumed that different vitals have different number of severity levels.

Figure 1C:
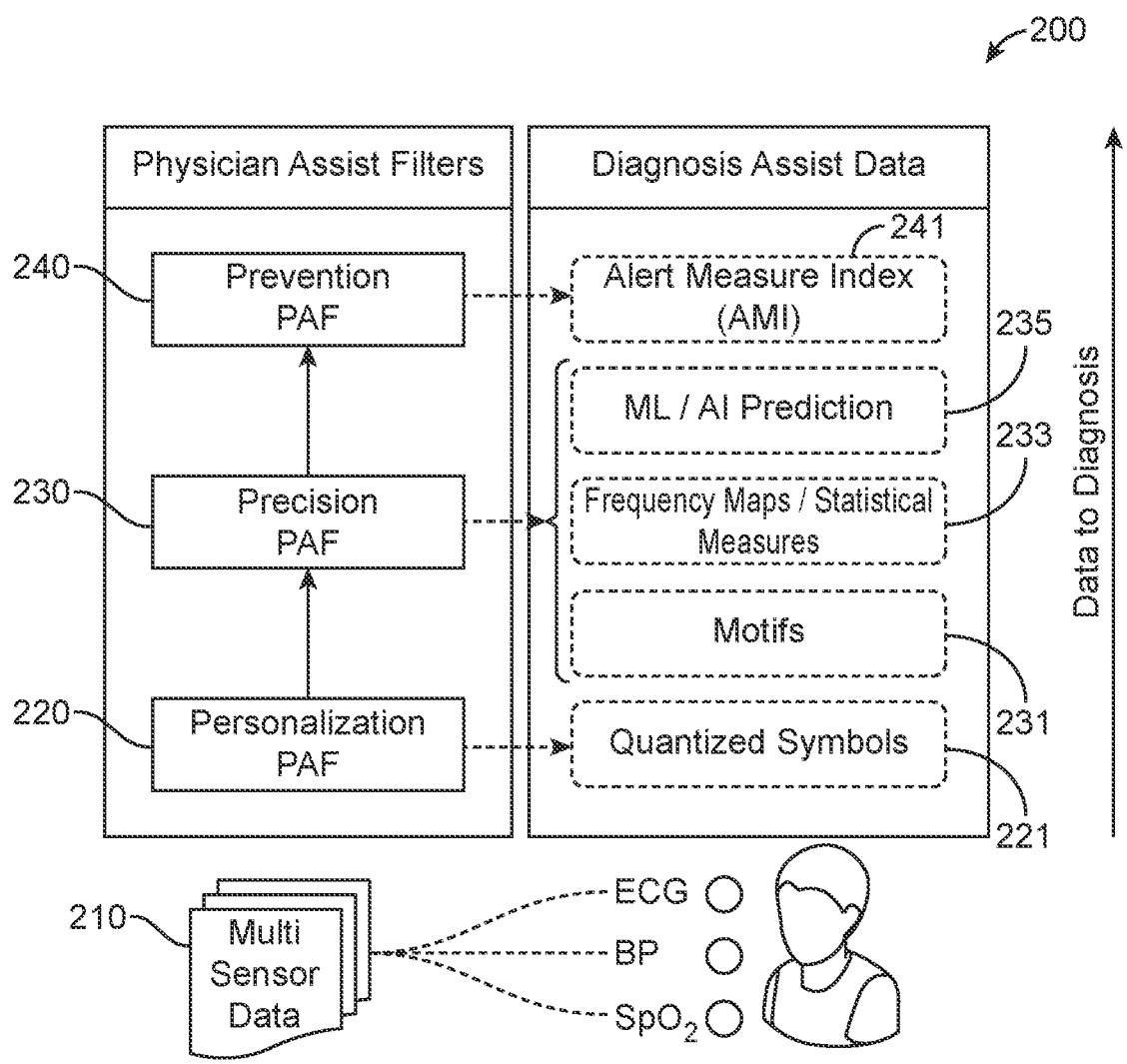
FIG. 1C shows PAF framework that progressively converts the raw multi-sensor data into quantized symbols, helpful motifs, diagnostic predictions and critical alerts.

In some embodiments, the method utilizes a physician assist filter (PAF) 200 as shown in FIG. 1C that includes a personalization PAF 220, a precision PAF 230 and a prevention PAF 240. The personalization PAF converts the multi-sensor values to quantized severity symbols 221 and stores it in a Patient Specific Matrix (PSM). The precision PAF 230 extracts consensus motifs 231, generates severity frequency maps (SFMs) 233 and includes a machine learning algorithm (ML) 235 that may diagnose the abnormality in a patient. The PAF further includes a prevention PAF that may generate an "Alert Measure Index" (AMI) 241 of the abnormality detected.

In various embodiments the quantized severity symbols are personalized for each patient through the personalization PAF 220. The quantized severity symbols are arranged into a Patient Specific Matrix (PSM) of N rows and W columns, where N is the total number of sensors being observed, and W is a time window in which the data is summarized. The value of W can be set by a physician or automatically derived based on the risk perception of that particular patient.

In some embodiments, precision PAF 230 includes extracting a Candidate Motif, μCNM [P] that is a temporally ordered sequence of quantized consensus normal symbols belonging to N rows that are selected from PSM of patient P. In some embodiments, a Consensus Normal Motif, μCNM [P] a candidate motif in which all values represent the normal severity level $\alpha_{NORM}$, that means each and every value, is equal to A is determined. α[p] includes the p-th quantized severity symbol in a row of the PSM, α[1], α[2], . . . , α[p], . . . , α[W]. In some embodiments the observation window of the PSM includes candidates C represented by $$C=\{\alpha[1],\alpha[2], \ldots \alpha[p], \ldots \alpha[W]\} \quad (1)$$

μCNM[P] is represented as:

$$\mu_{CNM}=\alpha_{CNS}[C_1],\alpha_{CNS}[C_2], \ldots \alpha_{CNS}[C_N]> \quad (2)$$

where $\alpha_{CNS}[C_1], \alpha_{CNS}[C_2], \ldots \alpha_{CNS}[C_N]$ represent consensus normal symbols.

In some embodiments, a Consensus Motif (CM) 144, μCNM[P] a candidate motif satisfying the following two conditions: its hamming distance from μNOR[n] does not exceed a physician prescribed sensor-specific near normality bound, dNOR[n] and, its total Hamming distance D(α[p], $\alpha_{NORM}$) from all other μCAN[n] is the minimum. ICON represents the observed patient-specific near normal trend, is determined. The consensus normal symbol is represented as $$\alpha_{CNS}[C_p] = \left\{ \begin{array}{l} \alpha[p]: D(\alpha[p], \alpha_{NORM}) < S[n]_{THRESH} \\ \sigma[p] is the lowest such candidate \in H \end{array} \right\} \quad (3)$$

where $S[n]_{THRESH}$ is the near-normal severity threshold.

$$\sigma[p]=\Sigma_{i=1}^{W}D(\alpha(p),\alpha(i)) \quad (4)$$

where σ[p] denotes the sum of Hamming distances of α(p) from α(i).

In some embodiments, a Consensus Abnormality Motif (CAM) 145, μCAM[P], a candidate motif satisfying the following two conditions: its hamming distance from $\alpha_{NORM}$ exceeds a physician prescribed sensor-specific near normality bound, dNOR[n] and, its total hamming distance from all other μCAN[n] is the minimum is determined. μCAM[P] is represented as $$\mu_{CAM} = \alpha_{CAS}[C_1], \alpha_{CAS}[C_2], \ldots, \alpha_{CAS}[C_N] > \quad (5)$$

where $\alpha_{CAS}[C_1], \alpha_{CAS}[C_2], \ldots \alpha_{CAS}[C_N]$ represents consensus abnormality symbol and wherein $$\alpha_{CAS}[C_P] = \begin{Bmatrix} \alpha[p]: D(\alpha[p], \alpha_{NORM}) \geq S[n]_{THRESH} \\ \sigma[p] \text{ is the lowest such candidate} \in H \end{Bmatrix} \quad (6)$$

In one embodiment, the prevention PAF generates an alert measure index (AMI) based on the severity level of the patient's abnormality. The AMI score may prioritize the patient The AMI is calculated as:

$$AMI[P] = \Sigma_{n=1}^{N} \theta[S_n][\mu_{CAM}[P][n]] * num(\mu_{CAM}[P][n])] \quad (7)$$

where $$\theta[S_n][\alpha] = \frac{K_1}{\Delta[\alpha]}$$

is a sensor and severity symbol-indexed matrix of weights derived using interventional time, $\Delta[\alpha]$ is intervention time and a is severity level.

Figure 1D:
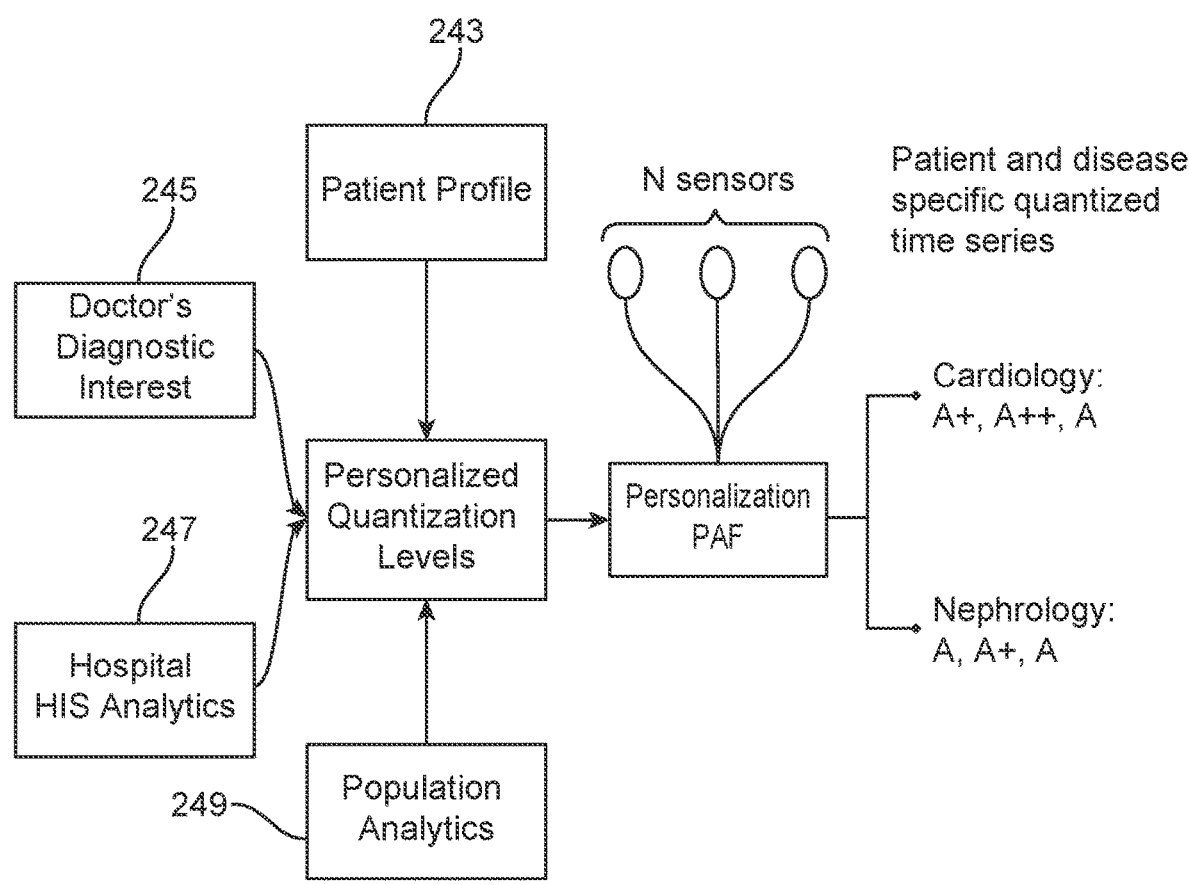
FIG. 1D illustrates quantization of sensor data based on multiple severity categorization criteria, resulting in the generation of patient and disease specific quantized values.

In one embodiment the quantization of sensor data as shown in FIG. 1D is based on multiple severity categorization criteria, resulting in the generation of patient and disease specific quantized values. In various embodiments, the multiple severity categorization criteria may be patient profile 243, doctor's diagnostic interest 245, hospital HIS analytics 247, population analytics 249. In some embodiments, the method includes connecting to the remote PAS, such as a cloud PAS. In some embodiments, the system can use a hybrid of ad hoc and infrastructure methods to connect to one or more of cloud PAS, the body-worn device or the mobile computing device. In other embodiments, when the infrastructure connectivity through mobile data network or Wi-Fi is unavailable, the mobile computing device can connect to other nearby mobile computing device in an ad hoc manner to deliver the data to the cloud PAS.

In various embodiments of the methods for use in the system, Health Service Personnel (HSP) access the data provided by cloud PAS or HIS PAS using web or mobile applications. In one embodiment, the HSP may include one or more of doctors, nurses, technicians, or emergency responders who analyze the data and take necessary steps. In some embodiments, emergency responders are configured to use the most reliable SoS communication channel from the available ones while responding to any contingencies.

In various embodiments, the methods implemented in the system provide mechanisms to analyze the sensor data coming from data aggregation and transmission unit to mobile computing device to conclude the usability of data. In some embodiments, methods to autocorrect data or retrieve error-free data using signal-processing techniques are also included. In certain embodiments, the method is a method of automatic detection of lead reversal in ECG signals and auto-correction.

Figure 2:
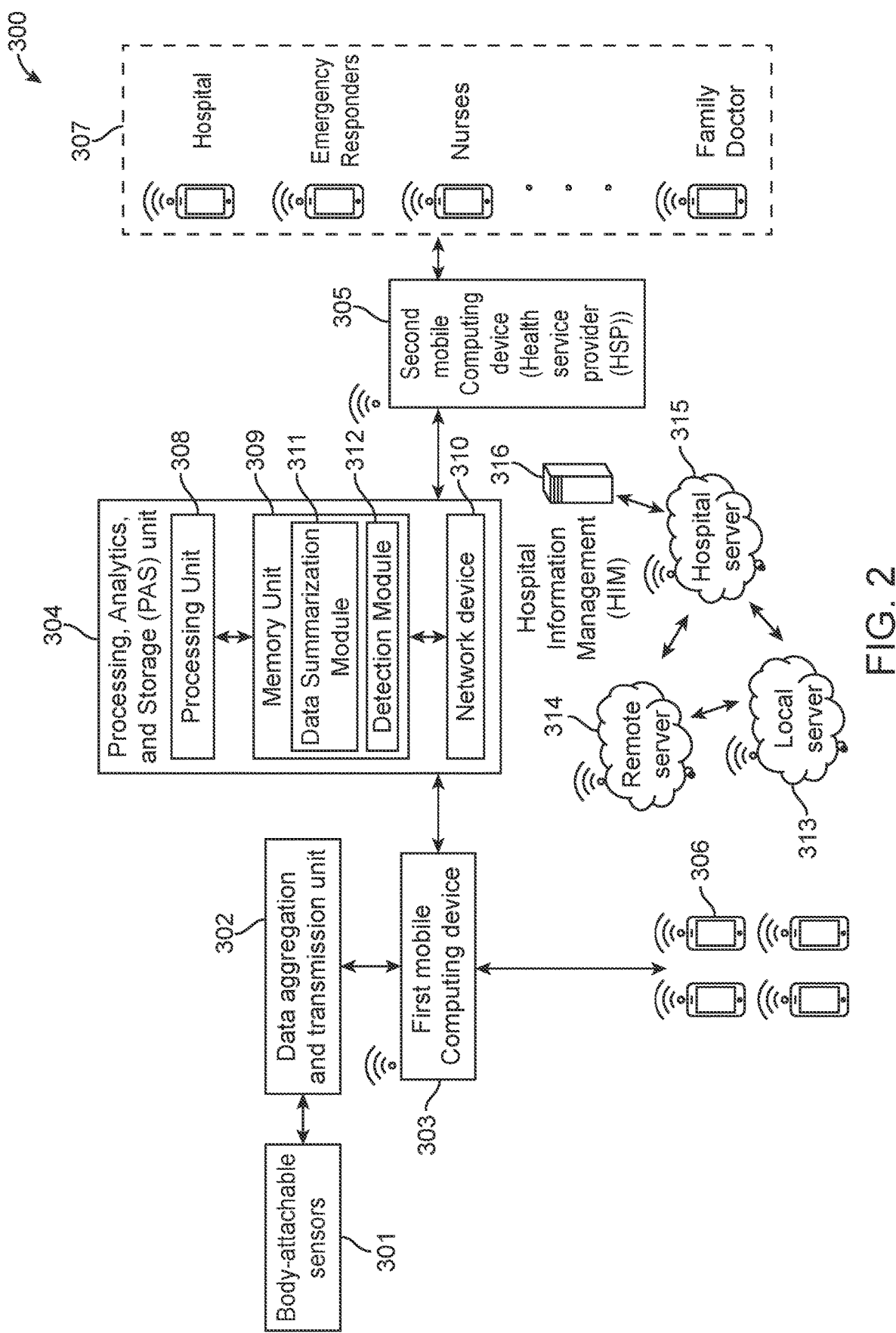
FIG. 2 shows a system for remote monitoring of a patient.

In various embodiments a system 300 for use in remote monitoring of a patient is disclosed. The system 300 as shown in FIG. 2 includes at least one sensor unit 301 attached to the patient's body to obtain sensor data of various health parameters, a data aggregation and transmission unit 302 that is interfaced with sensor unit 301 to receive the sensor data, a first mobile computing device 303 that is configured to receive and transmit the sensor data through a wireless communication network, at least one processing, analytics and storage (PAS) unit 304 that is configured to receive, analyze and store the sensor data from the first mobile computing device. In some embodiments the first mobile computing device 303, the PAS unit 304, or a combination thereof is configured to detect one or more abnormality in the sensor data, quantize a severity and identify if quantized severity exceeds a severity threshold. The system 300 further includes a second mobile computing device 305 that receives data from the PAS 304 and that may notify a Health Service Provider (HSP) in case of any severity exceeding the severity threshold. In various embodiments the data aggregation and transmission unit 302 is configured to notify the first 303 and/or the second 305 mobile computing devices when the quantized severity exceeds the severity threshold. In some embodiments the severity threshold for the patient is based on sensor data, inter-sensor correlation, patient's historical data, doctor's inputs, inter-patient machine learning models, or a combination thereof.

In some embodiments, the sensor unit 301 includes body attachable sensors for obtaining sensor data from physiological signal measurements. The sensor unit 301 may include at least one of a BP sensor that could measure the blood pressure level of the patient, a glucose sensor to sense the concentration of glucose in blood, a SpO2 sensor to measure the oxygen saturation level in a patient's hemoglobin, an ECG sensor that records the electrical activity of the heart, a motion detection system, an accelerometer or a GPRS.

In some embodiments, the systems and other components in FIG. 2 may be computing devices, such as servers, desktop computers, laptop computers, tablet computers, personal digital assistants (PDA), smartphones, mobile phones, smart devices, appliances, sensors, or the like. The computing devices may include processing units, memory units, network interfaces, peripheral interfaces, and the like. Some or all of the components may comprise or reside on separate computing devices or on the same computing device. In some embodiments, the devices may be configured to utilize various communication protocols, such as Global System for Mobile Communications (GSM), General Packet Radio Services (GPRS), Enhanced Data GSM Environment (EDGE), Code Division Multiple Access (CDMA), Wideband Code Division Multiple Access (WCDMA), Bluetooth, High Speed Packet Access (HSPA), Long Term Evolution (LTE), 5G, 5G-New Radio, and Worldwide Interoperability for Microwave Access (WiMAX).

In one embodiment, the first mobile computing device 303 is configured to transmit the sensor data through a GSM, 2G, 3G, 4G, LTE, Wi-Fi network or an Ad-hoc network created with neighboring wireless terminals or devices 306. In some embodiments the second mobile device 305 is configured to connect to other mobile devices 307. Mobile devices 307 may be associated with other health service personnel such as specialist practitioners, emergency responders, technicians, nurses, caregivers, and hospital administrators.

In various embodiments, each PAS unit 304 may be a computing device including at least a processing unit 308, memory unit 309, and/or network device 310. The memory unit 309 may include a data summarization module 311 and/or detection module 312. The data summarization module 311 may be configured to interpret a large amount of multi-sensor data and convert the data to form sequence of severity symbols or motifs. The severity symbols may be converted such that they are arranged in a patient specific matrix. In one embodiment, the system may include more than one PAS unit 304 with processing, analytics, and storing capabilities. For instance, the system may include multiple servers as PAS units 304, such as a local server 313, a remote server 314 and/or a hospital server 315 connected by a wired or a wireless network. In one embodiment, the hospital server includes a hospital information management (HIM) system 316. In various embodiments, the data aggregation and transmission unit 302 is interfaced with sensor unit 301 to receive the sensor data. The interfacing of the unit 302 with the sensor unit 301 could be either through wired or wireless connections. In some embodiments, the data aggregation and transmission unit 302 is a wearable device such as body-worn, small-form factor data collection, caching and/or dissemination unit that is connected to body sensors through a collection of wired and wireless media, for prolonged remote real-time monitoring of patients and/or in-ward telemetry.

In one embodiment, the system includes a mobile computing device 303 to receive, store, process, visualize, analyze and forward the data sent from the data aggregation and transmission unit. In some embodiments, the system additionally includes an application running on the device 303 for collecting location information of the user and the accelerometer reading from the device 303.

In various embodiments, the PAS unit 304 optionally includes one or more servers 313, 314, 315 and 316 that can receive, store, process, analyze and push data to mobile terminal 303 or 305 and associated application, which can visualize and present patient health status to doctors, hospitals, caregivers and emergency responders based on the criticality of the data.

In various embodiments, the PAS 304 is a local PAS module 308 based on a simpler algorithms for initial analysis and early warning dissemination of data. The local PAS 304 in some embodiments can also use the APIs provided by the cloud PAS to do complex PAS tasks and is connected over an existing infrastructure. In some embodiments, the mobile computing device 303, 305 or data aggregation and transmission unit 304 may also be integrated with a PAS module that incorporates PAS algorithms that may run as background services in the smartphone itself. In one embodiment, the system includes a complex PAS Layer that implements disease detection, big data analytics, complex storage policies and computationally intensive algorithms that are not possible to be implemented in local PAS due to its processing and power constraints. In various embodiments, the complex PAS is implemented through a remote server 313 or through a hospital server 315, or could be local to the hospital server such as a HIM 316. In some embodiments, hospitals might have different policies on patient data storage and processing. In these embodiments, a centralized storage and processing policy may not be used and the hospitals may access the services provided by the cloud PAS through APIs over existing infrastructure.

In some embodiments the data aggregation and transmission unit 302 includes one or more of a rechargeable body-worn hardware unit, sensors such as ECG, BP, SpO2, blood glucose sensors attached to the body and interfaced with the data aggregation and transmission unit over wired or wireless media. In some embodiments, the data aggregation and transmission unit 302 can continuously record sensor data and is configured to capture asymptomatic episodes of patient disease. In some embodiments, the data aggregation and transmission unit 302 is configured to tag sensor data as related to physiological symptoms using a button in the data aggregation and transmission unit. In some embodiments, the data aggregation and transmission unit 302 is configured to use voice based tagging of data in the smartphone which allows patients to speak about an event, which is tagged along with the sensor data. In some embodiments, the voice based tagging of data allows the patients to make specific complaints related to the event. In some embodiments, the data aggregation and transmission unit 302 is configured to send a SoS signal to the healthcare personnel in case of emergency conditions. In some embodiments, a motion detection system including an accelerometer is placed inside the data aggregation and transmission unit. In certain embodiments, the data aggregation and transmission unit 302 is connected to the patient's smartphone over a wireless network to transmit the raw data. In some embodiments, the data aggregation and transmission unit 302 is connected to the patient's smartphone over a short-range wireless network. In some embodiments, the smartphone has applications related to data analysis and processing. In some embodiments, the data aggregation and transmission unit 302 can also include an in-built GPRS module that can directly send data to the remote healthcare personnel's smartphone or a remote data reception unit.

In various embodiments, the sensors send the data to the data aggregation and transmission unit 302. The data aggregation and transmission unit 302 then forwards the data to the patient's smartphone or another mobile computing device 303 configured to perform computation and real-time processing. There can be multiple devices in the neighborhood 306. These devices can have varying capabilities and can be linked over a heterogeneous network, such as WiFi or Bluetooth. The patient's handheld device can also be connected to another patient or health service personnel (HSP), such as that of a doctor or a clinician. The handheld devices are connected to a server, such as a private or public server over different media and networks. In some embodiments, the server may be a cloud based server. The cloud has higher capabilities for batch processing than the handheld devices as well as large storage space for long term archival of data. The public and private parts of the cloud are also connected through proper interfaces.

In various embodiments, the data aggregation and transmission unit 302 and mobile computing device 303 are configured to communicate with each other and share their processing and storage capabilities, independent of the cloud PAS. In some embodiments, the patient's data is routed to the doctors' handheld device skipping the cloud PAS, thereby reducing the upstream traffic to the cloud PAS. In certain embodiments, the data archival in the cloud PAS is done later when the cost of transmission is lower. In these embodiments, the system architecture allows the handheld devices to go offline from the cloud PAS and then join in later through a different network.

Figure 3:
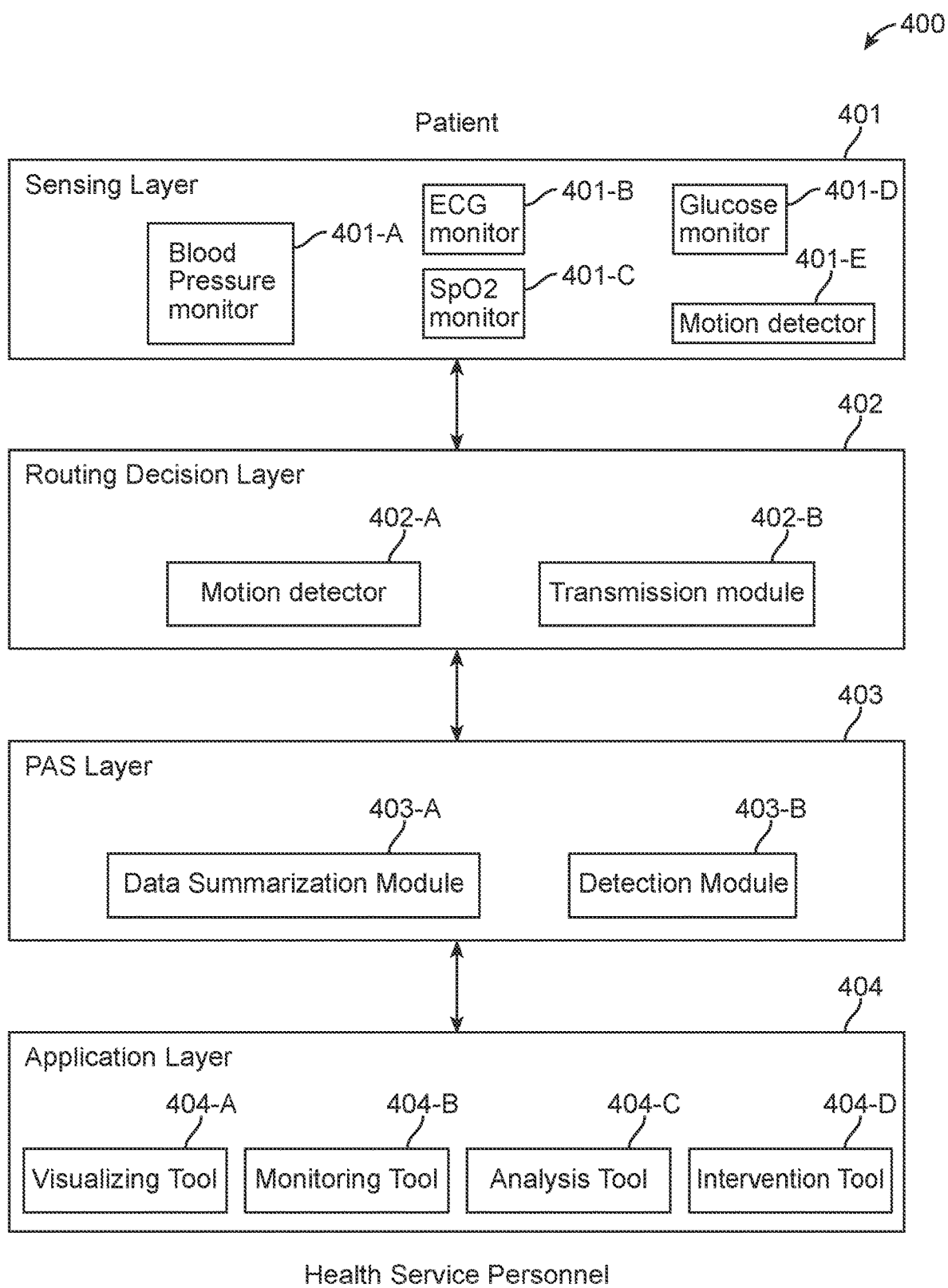
FIG. 3 shows a multilayer system communication and analytics architecture.

In various embodiments, the remote health monitoring system 300 of the invention includes architecture 400 as illustrated in FIG. 3. The architecture 400 may include one or more layers for performing the method 100. The layers include a sensing layer 401, a routing decision layer 402, a PAS layer 403 and an application layer 404. In some embodiments, the sensing layer 401 includes sensor modules for continuously monitoring at least one or more of sensors connected to the patient's body such as BP 401-A, ECG 401-B, SpO2 401-C, and glucose 401-D, as well as the user activity such as by using accelerometer motion detector 401-E. In some embodiments, the routing decision layer includes a data aggregator 402-A and transmission module 402-B. In some embodiments, both data aggregation and transmission is performed by a single unit such as a body-worn device connected over a short-range wireless network. The unit receives data from the sensors 401 and directly sends it to a first mobile computing device. In some embodiments, the Routing Decision Layer 402 performs three functionalities: a) to decide where and when the sensed data needs to be processed, analyzed and stored b) to decide the best routing path out of the available heterogeneous options c) to interface and exchange data with the nearby mobile device or data aggregation and transmission unit over ad hoc networks. The PAS layer includes data summarization module 403-A and patient data severity detection module 403-B that interprets a large amount of multi-sensor data and converts it to form sequence of severity symbols for subsequent processing. The application layer 404 in various embodiments includes various visual tool 404-A, monitor tool 404-B, analysis tool 404-C and intervention tool 404-D. Users of the second mobile device, such as hospitals, medical practitioners, nurses, etc., may be provided a graphical user interface in the application layer. The users may perform various actions including monitoring, analyzing, and intervening using the mobile device. In some embodiments, a wired Ethernet using existing hospital infrastructure connectivity is also utilized alternatively.

Figure 4:
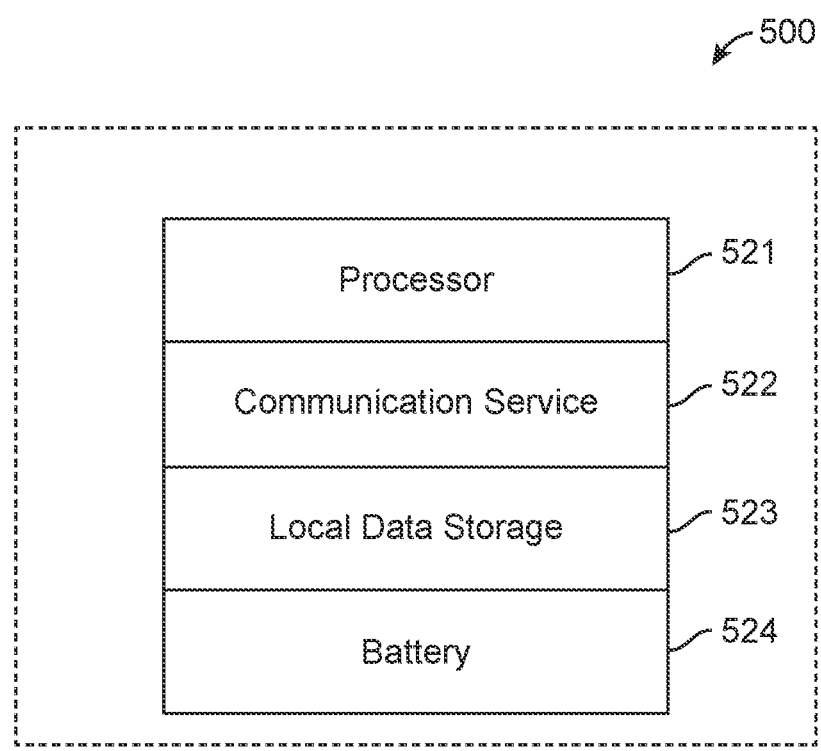
FIG. 4 shows a body-worn device for use in a system for prolonged remote real-time monitoring of a patient.

In various embodiments the data aggregation and transmission unit 302 for prolonged remote real-time monitoring of a patient is a body-worn device 500 as shown in FIG. 4. The body-worn device 500 includes at least one processor 521 configured to calculate MP-CAM and AMI, a wireless communication module 522, a memory or data storage module 523, and a power supply unit or battery 524. The device 500 is configured to receive inputs from the one or more body sensors 301 through wired or wireless connections. In some embodiments, the device 500 includes a hardware switch that may tag the received sensor data to related physiological symptoms. The device 500 may further include a motion detection system that includes an accelerometer. The memory module 523 is configured to aggregate data received from the one or more sensors 301. The wireless communication module 522 is configured to transmit the data to at least one of a remote server 314, or a mobile device 305. In some embodiments, the device 500 includes a built-in power management system to prolong the available life of the battery 524.

Figure 5A:
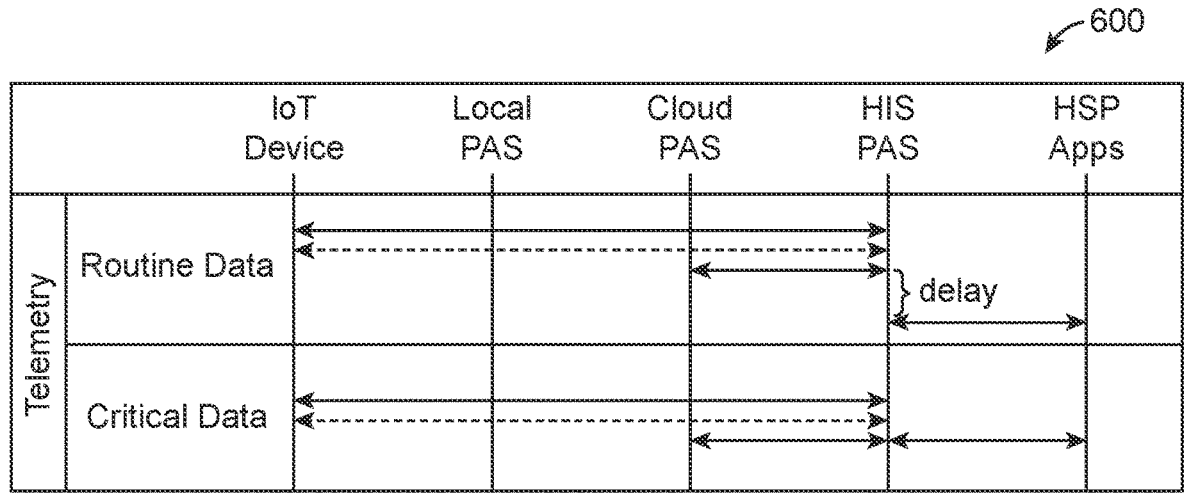
FIG. 5A shows a heterogeneous path selection mechanism for patients who are inside the hospitals, such as in-ward telemetry.
Figure 5B:
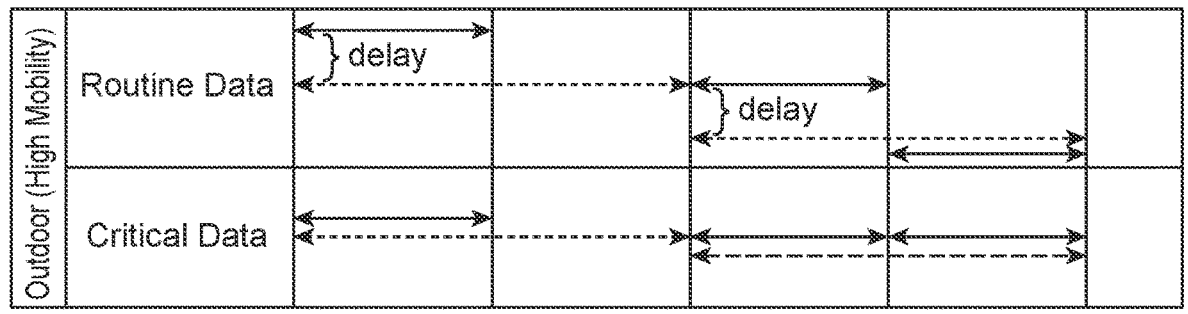
FIG. 5B shows a heterogeneous path selection mechanism for high mobility patients who are outdoor.
Figure 5C:
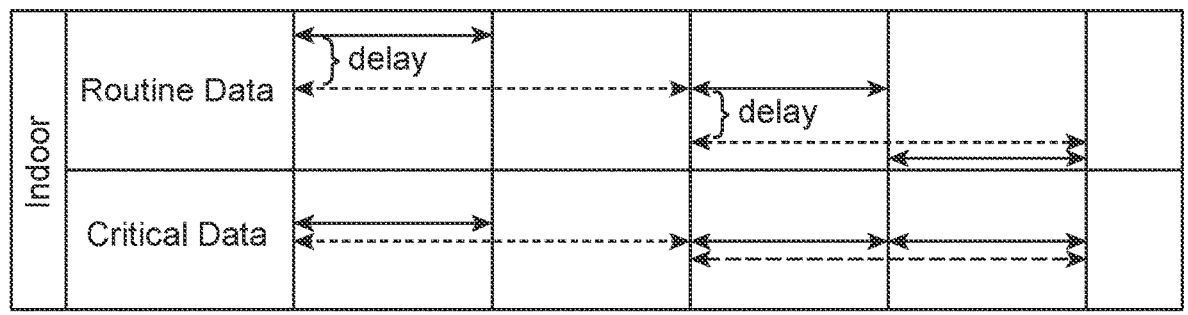
FIG. 5C shows a heterogeneous path selection mechanism for patients who are indoor.
Figure 5C:
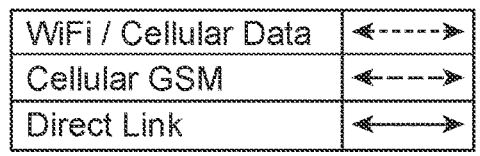

In one embodiment, the system includes prioritizing the communication based on a mechanism 600 as illustrated in FIG. 5A, FIG. 5B and FIG. 5C that considers a combination of user location using GPS or other localization techniques, mobility data via smartphone sensors, and health criticality of the patient to prioritize communication. Accordingly, in some embodiments, prioritizing mechanism 600 may send critical data via a higher priority channel such as a direct link or a cellular GSM. In some embodiments, the mechanism sends routine data using any available channel with a delay to minimize congestion or optimize bandwidth availability or both.

In various embodiments of the systems and methods disclosed herein, a reliable, low delay tolerant communication network is provided. The systems and methods envisage providing optimal network support in rural regions, where availability and reliability of networks is a challenge. In other embodiments, in urban settlements, methods such as selecting the least cost network, ensuring continuous bandwidth availability, etc., can also be incorporated. In case of highly mobile patients, the methods in some embodiments are configured to take into account frequent change in mobile base stations. In some embodiments, in addition to the above considerations, health data priority and patient context may also be used to optimize route selection.

In various embodiments, the priority of the data is determined from the type of sensing and the analysis results from local PAS. In some embodiments, two data priority levels, 1) routine data and 2) critical data are determined. In various embodiments, routine data is collected during routine sensing and acquisition scenario. In some embodiments, the routine data is sent to the local PAS if available from the mobile computing device or data aggregation and transmission unit, and the method envisages classifying the data as routine or critical. In one embodiment, based on the result of local analytics, if the vital measurement shows variations from normal level, it is tagged as critical. In another embodiment, if the data does not show any significant variations, it is stored in the mobile computing device or data aggregation and transmission unit cache and transmitted at a later time over a non-time critical path. In some embodiments, if the mobile computing device or data aggregation and transmission unit do not have connectivity to a local PAS, they transmit the data to the complex PAS layer. In embodiments where the data is classified as routine data and therefore not of immediate use by the HSP, a delayed transmission through non-time critical route is adopted and the routine data is accessed by the HSP at a later point of time.

In some embodiments, the data is classified as critical data if it consists of data collected during patient or doctor triggered sensing. In some embodiments, the method includes sending the data to the local PAS and analyzing for any deviations from normal values before deciding the routing path. In some embodiments, in the absence of a conclusive result from the local PAS (or even non-availability of local PAS), the data is transmitted to the complex PAS through a time-critical route and then notified to the HSP immediately in order to help them make emergency interventions.

In some embodiments, the system includes use of one or more applications of remote health services for patients who are inside the hospitals, such as in-ward telemetry as shown in FIG. 5A when a patient needs to be monitored after a critical operation. In some embodiments, the system includes monitoring patients who are discharged from the ICUs to general ward by a HSP. In some embodiments, the mobile computing device or data aggregation and transmission unit communicates with the existing hospital infrastructure using Wi-Fi or wired Ethernet connection. In some embodiments, a reliable low cost route to reach the HIS PAS is utilized and the mobile computing device or data aggregation and transmission unit need not send the data to a local PAS. In other embodiments, a communication framework which is able to deliver all the services through a highly reliable, high bandwidth WiFi or direct link connection is provided. In some embodiments, the HIS PAS may communicate with the cloud PAS through APIs for various needs through a high bandwidth link, which is part of an existing infrastructure. In other embodiments, an indoor routing policy is adopted in the absence of a reliable hospital infrastructure.

In some embodiments, the monitoring is outdoor monitoring as shown in FIG. 5B. In certain embodiments, the system includes transmitting the data to the cloud PAS based on the data priority from the mobile computing device or data aggregation and transmission unit. In some embodiments, a combination of cellular data and Wi-Fi are used when selecting a time critical route, if the mobility pattern is already known. In alternate embodiments, a route based on GSM is used when selecting in the absence of a known pattern. In some embodiments, the transmission of routine data is delayed till the device reaches an indoor environment from the mobile computing device or data aggregation and transmission unit. In other embodiments, the mobile computing device or data aggregation and transmission unit can opt to search for an IoT gateway over an ad hoc network.

In some embodiments, the monitoring is indoor monitoring as shown in FIG. 5C. In certain embodiments, the framework includes routing policy assumes that the issues of switching cellular base stations and WiFi networks does not arise as much compared to an outdoor location. In some embodiments, the routing path is decided from the results generated in the local PAS by forwarding the data from a mobile computing device or data aggregation and transmission unit. In some embodiments, the data is transmitted over Wi-Fi or cellular data network, even in critical situations and a GSM based route is not required unless other options are unavailable. In some embodiments, the mobile computing device or data aggregation and transmission unit can form ad hoc network with other mobile computing device or data aggregation and transmission unit and send the data through the gateway device in the absence of an infrastructure to access internet.

In sensor networks, power is a major consideration to decide the frequency of sensing, data processing, route selection and transmission frequency. In some embodiments of the invention, the architecture allows taking these decisions at both the mobile computing device and data aggregation and transmission unit.

In some embodiments, the framework includes defining a power policy 700 defined based on the different levels of available battery power, as illustrated in FIG. 5D. In some embodiments, the devices are usually attached to or near the user and the devices are recharged at least once in a day if required.

In some embodiments, each sensor has different sensing frequencies. In one embodiment, the method includes measuring BP and blood glucose only twice or thrice in a day. In some embodiments, the patient is on continuous ECG monitoring and the sensor transmits the data continuously. In some embodiments, there is difference between the sensing and transmission energy requirements for different sensors. In additional embodiments, the method includes defining the available battery power of devices and sensors as the time up to which it can carry out of sensing and transmission. In some embodiments, the absolute values given can be altered according to different usage scenarios using a power management mechanism based on available battery power, the data priority and location of the patient.

In some embodiments, the system includes defining the available power as low, medium and high as shown in FIG. 5D. In some embodiments the available power is defined as low, when there is only enough battery power to sense and transmit for below three hours. In other embodiments, the device has to be recharged within a specified time, to ensure continuous sensing and data availability. In some embodiments, the available power is defined as medium, when there is enough battery power to support sensing and transmission between 3-12 hours. In some embodiments, the available power is defined as high, when there is enough battery power to support sensing and transmission between 12-24 hours.

In certain embodiments, the system includes a framework capable of immediately transmitting the data (specified as "Immediate"). In some embodiments, the method includes a framework capable of storing and sending (specified as "Delayed") at a later point of time, when the battery level improves. In yet other embodiments, the method includes a framework capable of sending the data to the local PAS for processing (specified as "Local PAS"). In some embodiments, the delayed transmission results in conserving available resources while the Immediate and local PAS results in higher battery drain. In some embodiments, it is assumed that the power requirements for local PAS is much less compared to the transmission cost to the cloud PAS.

In some embodiments, network selection plays an influential role in the context of power management. In some embodiments, the transmission power for different media varies. In some embodiments, the power management policy is to select the least power-consuming medium. In other embodiments, the health context of the patient also needs to be factored in. In some embodiments, the power management policy includes a three-level decision mechanism that includes selecting a subset of paths based on the routing policy, deciding on processing, transmission, and storage based on the battery level, and choosing from one or more medium options for transmission, the medium with the least power requirements.

In one embodiment, the routing and power policies are firmly based on reliable delivery of relevant health data to the HSPs. In some embodiments, the routing and power policies are based on the patient context, which includes his health status, activity and location, to dictate which path to be taken and when the data needs to be transmitted. In one embodiment, the critical data is always transmitted, while routine data is transmitted at a later time. In another embodiment, the path selection is based on power policy and location and results in conserving battery.

In some embodiments, a sensor signal quality analyzer is included to detect if the sensor signal received is usable data. In other embodiments, an auto-correction algorithm is included to retrieve the original signal from the unusable signal for correction of human errors such as lead misplacement in ECG signals. In some embodiments, a patient feedback system that provides automated feedback to the patient regarding signal quality and suggestions to improve by changing the placement of the sensors or adjusting other physical parameters of the body sensors is included. In some embodiments, a primary patient condition analysis based on thresholds of the sensor signals that can tag the data as critical, non-critical or of unknown-criticality is included. In some embodiments, a data compression and storage mechanism for temporary storage of data in the smartphone is included. In other embodiments, a data transmission mechanism to send data to the healthcare personnel and the cloud is included. In one embodiment, an algorithm to decide the data transmission based on the availability of the mobile and data networks, cost of transmission, the power availability in the device and the criticality of data is included. In another embodiment, the mobile computing device includes a data visualization mechanism whereby the patient or caretaker can see the sensor data received in real-time on the smartphone.

In one embodiment, the method includes voice tagging of medically relevant physiological conditions or events. In one embodiment, a patient can tag the data using the button provided in the data aggregation and transmission unit or mobile computing device voice tagging capability using the microphone and using a user trigger in the device. In one embodiment, the method includes running a background service that constantly reads data from the data aggregation and transmission unit. In some embodiments, the method includes configuring the data aggregation and transmission unit using the smartphone. In other embodiments, the method includes visualizing various parameters of the data aggregation and transmission unit such as battery status and connectivity of body sensors.

In some embodiments, the system includes a decision support system (DSS) to detect abnormalities in sensor data used for prognosis and decision support for the HSP. In one embodiment, the system includes a DSS based on the capabilities of a mobile computing device and PAS. In other embodiments, preliminary DSS algorithms run on the mobile computing device while more complex DSS algorithms run on the PAS unit, such as a remote cloud server. In some embodiments, the system is configured to transmit the results of the DSS to the smartphone of HSP using the mobile computing device or PAS. In other embodiments, the system is configured to send alerts to the smartphone of HSP based on the severity of DSS results using SMS or GSM network along with cellular data or internet.

In some embodiments, the wearable device is configured to intimate relatives, HSP, or both in case of an emergency. In some embodiments, the method includes capturing of ECG, blood pressure, blood glucose, pulse rate, blood oxygen, and other vital parameters, and recording of data following a distress in patient as well as relatives, HSP, or both of the patient condition. In some embodiments, the method includes a SoS protocol for communication between the data aggregation and transmission unit, mobile computing devices and PAS, wherein the mobile computing device will act as a gateway to send emergency signals to remote hospitals along with the location of the patient. In some embodiments, the system is configured to transmit live stream of vitals during emergencies using GSM network or internet.

In some embodiments, the system includes enhancing patient management through a collective decision making process by utilizing doctors from multiple specialties who consider various physiological, pathological and other patient parameters and come to their own specific conclusions, which are then discussed to arrive at a patient management plan. In one embodiment, a cardiologist may set patient and disease specific quantization levels from a sensor. In some embodiments, the cardiologist sets the ST elevation or depression alert levels to identify emergency episodes of myocardial infarction in high-risk cardiac patients. In some embodiments, the alert levels are coupled with the context of the patient. In one embodiment, the threshold level is set lower in sedentary workers when compared to sport persons or high activity patients with higher threshold levels for emergency and early detection. In another embodiment, the BP, heart rate (HR) or SpO2 severity levels are set for identification of long-term trends in obstructive sleep apnea. In yet another embodiment, the HRV, RRV, and BP severity levels are defined differently for detection and tracking of chronic obstructive pulmonary disease (COPD).

In one embodiment, a neurologist sets a patient and disease specific quantization levels from a sensor. In some embodiments, the severity levels of BP and pulse rate are set as a combination to alert the practitioner of a discrepancy between BP and pulse rate for the occurrence of autonomic neuropathy, one of the major risks seen in epileptic patients. In one embodiment, if the difference between BP and pulse rate is not above a given threshold, the doctor may set the quantization level such that emergency alerts are sent to them.

In another embodiment, an endocrinologist sets a patient and disease specific quantization levels from a sensor. In one embodiment, a continuous blood glucose monitoring in high-risk patients is adopted to avoid complications arising out of hypo and hyper-glycaemia. In one embodiment, the severity levels is set based on blood glucose measurements over a long time interval depending upon the risk of the patients to prevent fatal events.

In another embodiment, an obstetrician sets a patient and disease specific quantization levels from a sensor. In one embodiment, continuous monitoring of fetal heart rate, mother's blood pressure, or both is done for early detection of any complications in high-risk pregnancies, which pose a severe threat to the mother and the child. In one embodiment, the obstetrician sets the severity quantizer level according to the specific condition of the mother and the fetus.

In some embodiments, the individual practitioners set patient and disease specific quantization levels from sensors, which are different from each other. In yet other embodiments, all practitioners may set severity levels of vital parameters in the same way, while specialized sensor severity levels may differ based on the patient. In some embodiments, the system is configured to utilize a RASPRO summarization technique and the associated algorithms.

While the invention has been disclosed with reference to certain embodiments, it will be understood by those skilled in the art that various changes may be made and equivalents may be substituted without departing from the scope of the invention. In addition, many modifications may be made to adapt to a particular situation or material the teachings of the invention without departing from its scope. Further, the examples to follow are not to be construed as limiting the scope of the invention which will be as delineated in the claims appended here.

EXAMPLES

Example 1: A Method for Determining CM and CAM

Using the comparison of individual data points as illustrated above, A*1 is compared with A*(1+l), A*(1+(2×l)) etc. In the problem of CM and CAM discovery in SSM, we assume l=f. The first row of sequences is compared with the other rows in a temporally ordered row wise comparison. To discover CM and CAM in SSM, a Hamming distance based algorithm was used as illustrated here:

```
Input: SSM
Initialize:
L = f; HammingDistMat = [0, ]W×W; dNOR [0]W×1; SumMat [0]W×1;
CM_Index = 0; CAM_Index = 0;
Procedure: FindHammingDistances
for i = 1 to W
for j = i to W
HammingDistMat [i, j] = HammingDist (SSM [i], SSM [j])
HammingDistMat [i, j] = HammingDistMat [j, i]
dNOR [i] = HammingDist (SSM [i], MNOR)
end for
end for
for i = 1 to W
SumMat [i] = sum (HammingDistMat [i, ...])
end for
Procedure: FindCM
for k = 1 to W
index = find_K-th_minimum (SumMat, k)
if (dNOR (index) ≤ α)
```

```
CM_Index = index
break
end if
end for
Procedure: FindCAM
for k = 1 to W
 index = find_K-th_minimum (SumMat, k)
 if (dNOR (index) ≥ α)
 CM_Index = index
 break
 end if
end for
Output: CM = SSM (CM_Index); CAM = SSM (CAM_Index)
```

First, the hamming distance of each of the $M_{CAN}$s from each other is determined followed by calculating their sums. The resulting summation matrix (Summate) along with the $d_{nor}$ matrix is used to find CM and CAM. For CM discovery, only those MCANs with $d_{NOR}$ less than a are considered while for CAM discovery those above a are used. Finally, an iterative method to find the index of the MCAN with k-th minimum sum of hamming distances from SumMat gives the CM and CAM index in the SSM.

Example 2: A Severity Quantization Technique for Continuous ECG Monitoring

Figure 6A:
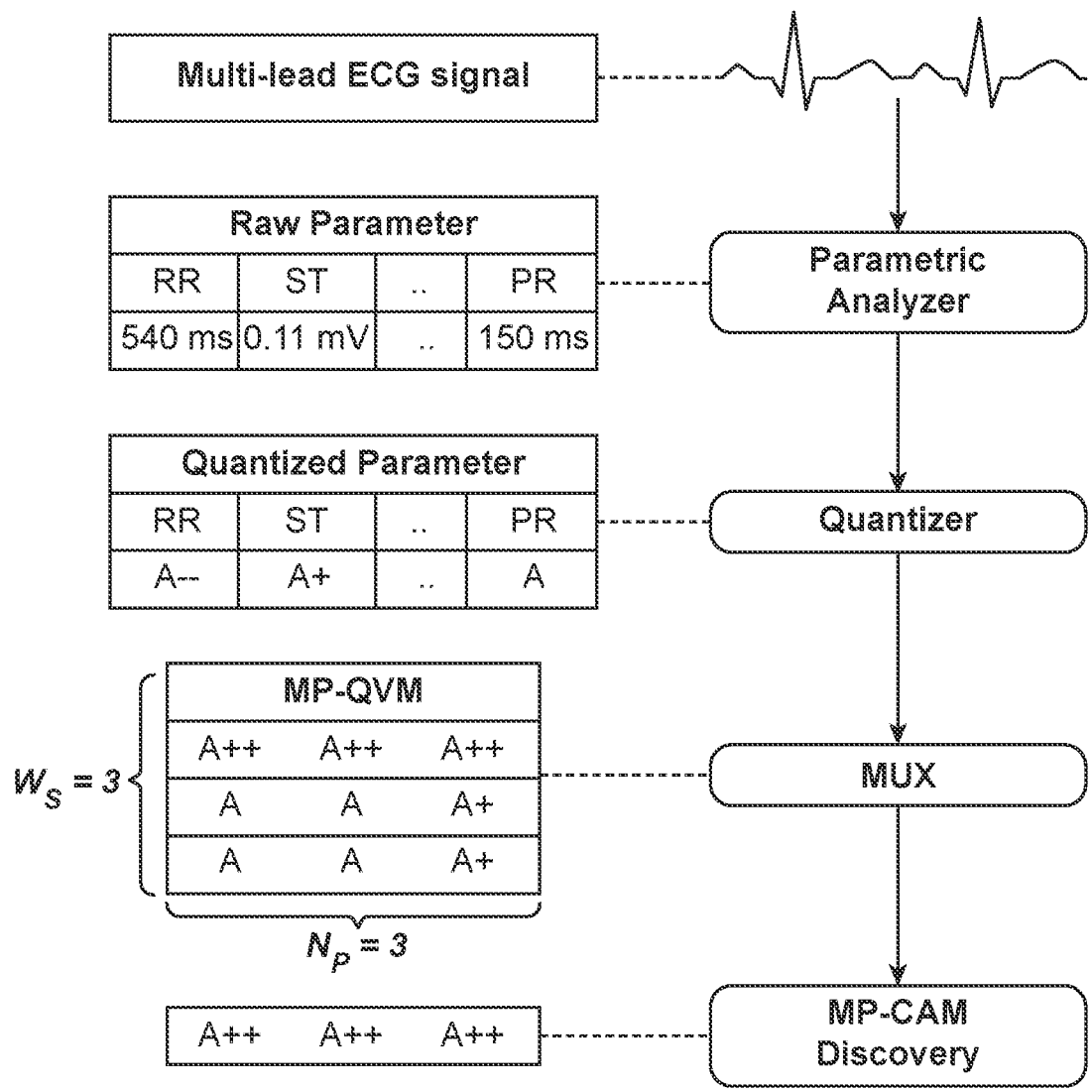
FIG. 6A shows a method of computing the Multi-Parameter Consensus Abnormality Motif (CAM) from raw sensor data.

A continuous monitoring ECG sensor as shown in FIG. 6A, SN is utilized. Suppose we intend to monitor a number of different parameters, P1, P2, Pi, such as RR interval, ST deviation, ST segment etc. Let us also assume that the total number of parameters is NP. The multi-parameter data is summarized and any criticality is identified such that a lucid report is sent to the doctors. Before abnormalities are found, the sensor data is preprocessed as follows.

First, the raw sensor data is processed by the parametric analyzer, which calculates the values of each parameter Pi, at a frequency of fP. Next, these parameter values are quantized into any of K severity symbols defined for the respective parameters (by the severity quantizer). The severity symbols are assigned as A+, A++, A−, A−− etc., based on the deviation from the medically accepted normal parameter value, which is denoted by the symbol A. The + and − symbols represent varying degrees of above-normal and subnormal severity levels. After this, the quantized values are sent to a mux, which constructs a multi-parameter quantized value matrix (MP-QVM). The columns of MP-QVM represent the different parameters, while the rows are time ordered quantized values. We describe a sample scenario below.

Suppose we need to discover a Multi-Parameter CAM (denoted as MP-CAM) once in every ten minutes, denoted as summarization frequency fS=1/600 (per sec). Assuming the parametric analyzer frequency fP=1 Hz, we discover CAM from an MP-QVM of 1/fS rows (denoted as observation window size WS) and NP columns. Next, the CAMs are discovered as discussed in the above section.

Interventional Time-Inverted Alerts: Alert Measure Index: At the end of each observation window (Dr, in an SSM, for every patient, we define an aggregate alert score, called the Alert Measure Index (AMI). The AMI is derived from the severity symbols, combined with severity specific weights and sensor specific weights. One of the embodiments of this AMI could be modeled as below:

$$\text{AMI}[\Phi] = \Sigma_{i=1}^{N} W[i] * \Sigma_{j=1}^{F*I} \text{num}(\mu_{CAM}[i][j]) * \Theta[j] \tag{8}$$

Figure 6B:
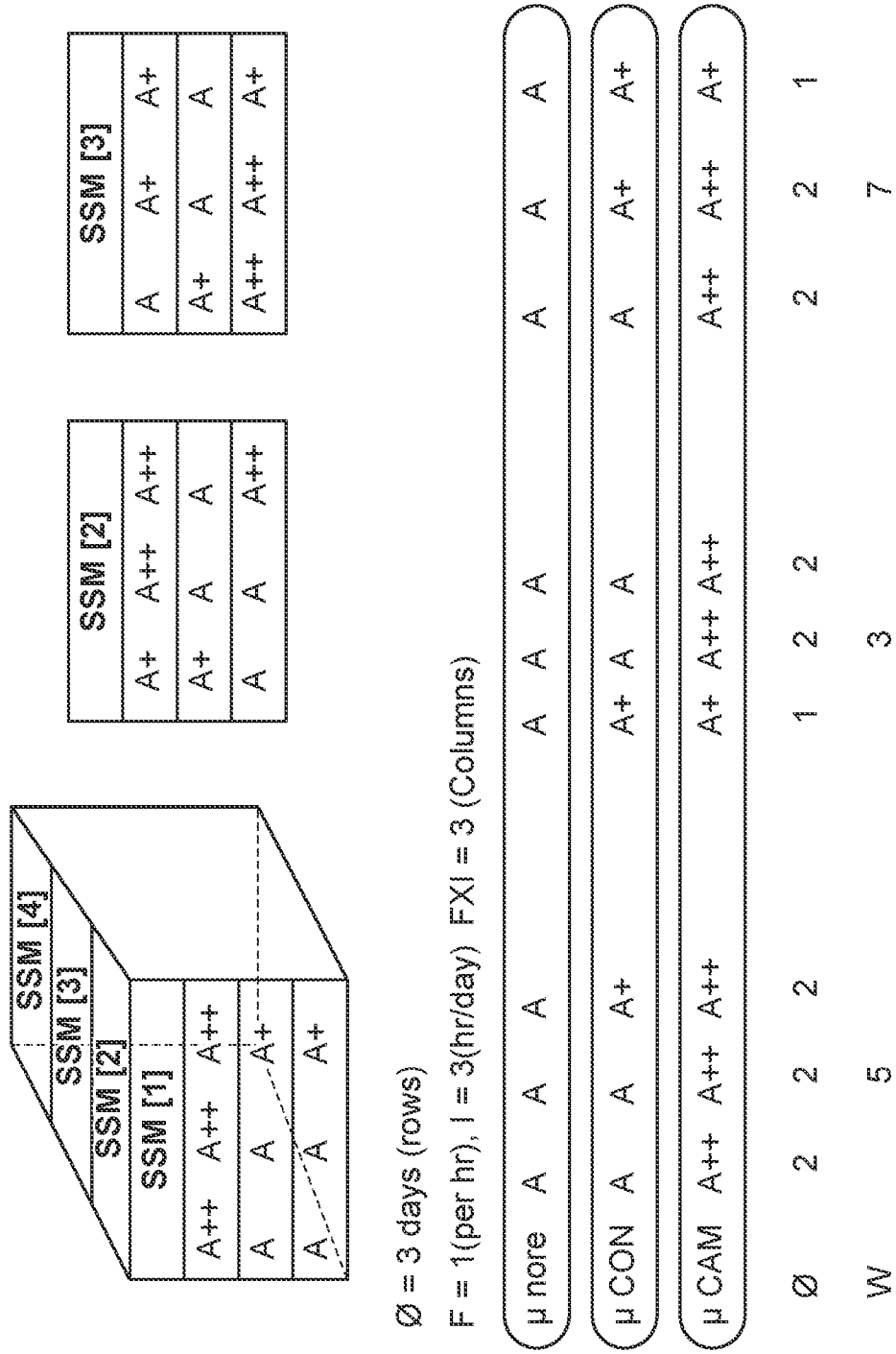
FIG. 6B shows a method of using Motifs to find the aggregate AMI score.

Wherein, the inner summation takes each severity value in the $\mu_{CAM}$ of the $i^{th}$ sensor, converts it into a numerical value (e.g., A± is assigned 1, A++/−− is assigned 2), scales it up by a severity specific factor Θ[j], and the outer summation scales it up by a sensor specific weightage W[i], both of which are derived from medical domain expertise, as illustrated in FIG. 6B. We call these two factors W and Θ as severity factors, and the resulting AMI is indicative of the immediacy of patient priority for physician's consultative attention.

We propose a goal directed approach to determining the severity factors W and Θ. The goal of delivering the alerts to the physician is to indicate the upper bound on the time that can elapse before which the physician's intervention is imperative to pull the patient out of danger. In order to capture this, we define the severity factors W and Θ as follows:

$$\Theta[\alpha] = \frac{K_1}{\Delta[\alpha]}, W[n] = K_2 / \Delta[n] \tag{9}$$

where, Δ[α] is the upper bound on the time for intervention for severity level α (which can take on values A++, A+, etc.), Δ[n] is the upper bound on the time for intervention for sensor n. In (2), constants K1 and K2 can be set by the physician considering the context of patient's health condition (including historical medical records and specific sensitivities and vulnerabilities documented therein). The inverse linear equation relating the severity factor to interventional time may be substituted with more complex equations for progressively complicated disease conditions. For instance, cardiologists prefer an exponential increase in alert levels if the monitored patient's ECG shows significant ST level depression: a direct indicator of myocardial infarction.

$$\Theta(\alpha) = e^{\hat{}}((K_1/(\Delta(\alpha)))) \tag{10}$$

AMI based frequency modulation: AMIs also serves as a feedback mechanism to modulate sensing frequency and alert computation instants. A low AMI is used to effect three adjustments: (1) Reduce the frequency F of future sensor measurements to a medically allowed minimum bound, (2) Increase the gap Γ between successive monitoring intervals, and (3) Increase the subsequent inter-alert window φ, thereby saving power and bandwidth of transmission. Similarly, a high AMI causes F to increase, Γ to decrease, and φ to increase. One of the embodiments of this adaptive frequency modulation can be modeled as below:

$$F_{r+1} = F_r[1 + C1*(\text{AMI}(\phi r) - \text{AMI}(\phi r - 1)] \tag{11}$$

$$\Gamma_{r+1} = \Gamma_r[1 - C2*(\text{AMI}(\phi r) - \text{AMI}(\phi r - 1)] \tag{12}$$

$$\phi_{r+1} = \phi_r[1 - C3*(\text{AMI}(\phi r) - \text{AMI}(\phi r - 1)] \tag{13}$$

where, C1, C2, C3 are positive feedback constants adaptively set by physician's preferences. A very high frequency causes redundancy in summarization while a lower frequency may result in missing sudden short duration spikes in parameters. An optimum frequency has to be specific to the patient, sensor and severity.

Figure 6C:
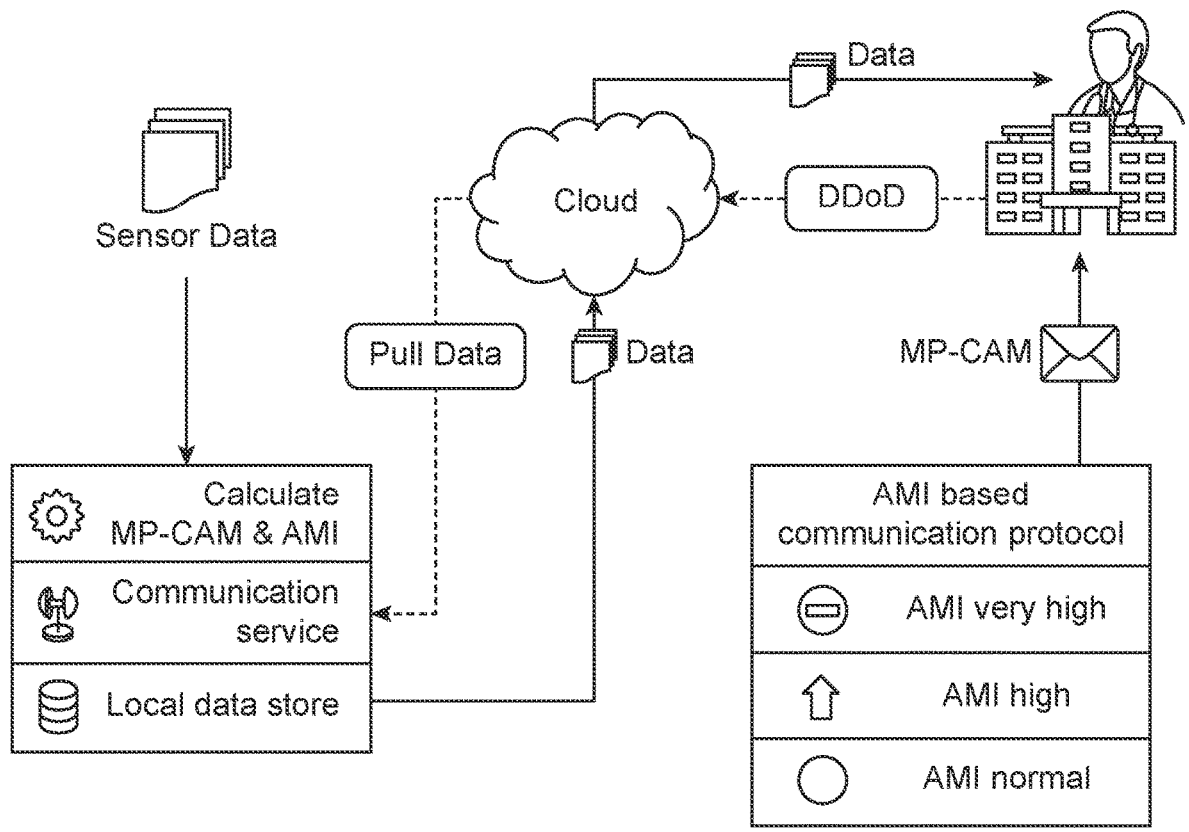
FIG. 6C illustrates a system and a method of calling data from the patient sensors according to perceived severity of the patient, through a technique called Detailed Data-on-Demand (DD-on-D).

Detailed Data on Demand (DD-on-D): Upon viewing the received AMI and CAM pertaining to a patient, the doctor may initiate a data pull mechanism, abbreviated as "DD-on-D" originating from the doctor's device to the cloud, as shown in FIG. 6C. The DD-on-D may further propagate to the patient's smartphone if part or whole of the data requested is still remnant on the patient's smartphone. The response to this request may trigger spontaneous switching on of the smartphone data if connectivity is available, and if not, refined summaries are transmitted via successive sequence of SMSs or MMSs. The DD-on-D also handles other data related directives from the doctor, such as a request to increment (or decrement) the summarization frequency, so that he/she receives CAMs more (or less) often from that particular patient.

Example 3: A System for Remote Monitoring of Vital Parameters in Patients

Figure 7:
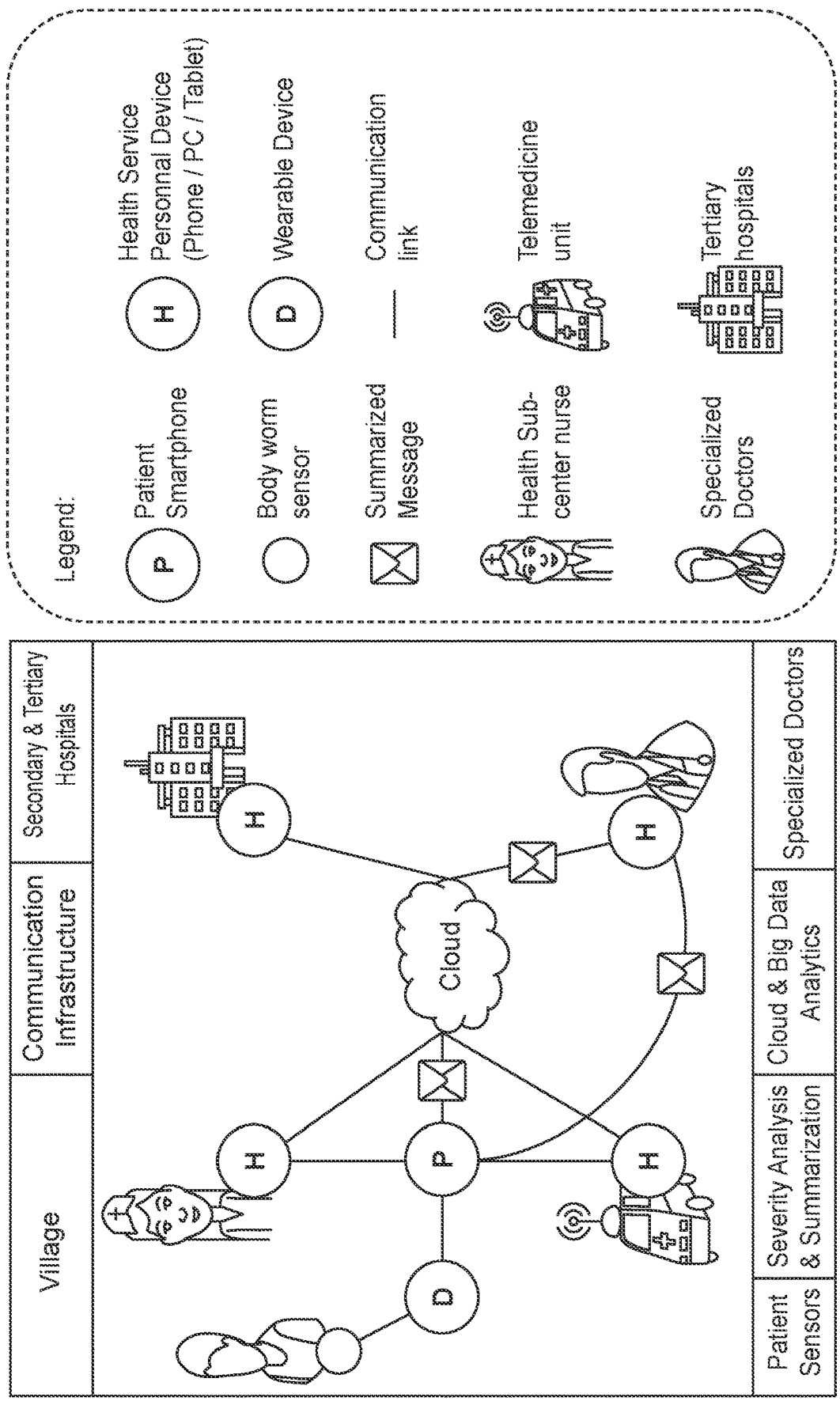
FIG. 7 illustrates a system for remote monitoring of vital parameters in patients.

A single sensor (ECG sensor) was used an example, as illustrated in FIG. 7. The system supports multiple sensors in a similar manner. A low power wearable device with 2 to 4 electrodes was attached to the body of the patient. The power management includes a buck-boost voltage regulator, a battery charge controller, and a battery fuel gauge. The main controller is an MSP430 microcontroller with SPI, ADC, I2C, timers and GPIO. An optional temperature sensor provides the body temperature monitoring. An extremely power sensitive firmware controls this device and manages its connectivity to the mobile phone.

A number of patients are remotely monitored through the system by a number of doctors and/or nurses. Each patient is provided with a wearable, battery-powered, and wireless data aggregation and transmission unit, which is worn as a necklace or placed on the waist. The body sensors are connected to the data aggregation and transmission unit using wireless connectivity. The wearable data aggregation and transmission unit connects to a PAS unit through the patient's smart phone, which is connected to the internet through 2G, 3G, or Wi-Fi network. The smart phone does a preliminary analysis to warn the patient of abnormalities, if any, specifically when internet connection is unavailable. The analytical storage engine of PAS unit does the backend storage and the signal processing of the acquired live signals before performing the required analytical diagnostics algorithm over the stream data. The server intimates the doctor, patient and the hospital monitoring service about the potential abnormality in the sensor signal. The doctor/hospital monitoring station may choose to connect to the server for the live sensor stream on their smart phone, tablet, or on a browser based web client. The doctor could further trigger an alarm to the patient about the criticality of his condition and further course of action.

Example 4:—Evaluation of the Effectiveness of the RASPRO System

We measured both the diagnostic ability as well as the preventive predictive power of the RASPRO technique of rapid summarization for effective prognosis in wireless remote health monitoring. We formulated three hypotheses, Personalization Hypothesis, Precision Hypothesis, and Prevention Hypothesis and evaluated the effectiveness of RASPRO in satisfying these.

Dataset: The first step to evaluate these hypotheses was to identify datasets that are extensive, long term and critically significant. We used large time series dataset from MIMIC II database, which contains multiple body sensor values from over 20,000 ICU patients. This dataset consists of ECG, ABP (Arterial Blood Pressure), HR, Non-obtrusive BP (NBP), SpO2, Mean Arterial BP (MAP), and other vital signs. From this, we selected a curated set of patient and control group data that contained a long time series data followed by a critical event.

We selected patients with Acute Hypotensive Episodes (AHE), which is a potentially fatal condition, found quite common in ICUs as well as caused due to postural hypotension. An AHE event is analytically identified as when MAP measurements remain below 60 mmHg for more than 30 minutes. This is a potentially fatal event and requires immediate intervention. We also made sure that the dataset provides uninterrupted MAP, and HR signals with a minimum sampling rate of 1 per minute, over at least 3 hours for both the event-patients as well as the control group. We selected a group of 30 patients (called group H) who had AHE during some time during their stay in ICU, and another 20 patients (called group C) who did not have AHE during their ICU stay. This dataset was selected from the PhysioNet challenge 2009. The H dataset also had a time marker to, after which AHE occurred in that patient within a one-hour window. Since the data was obtained from publicly available sources, we did not require getting prior approval of IRB for this work.

Evaluating Precision Hypothesis: The H and C group time series data comprising of Mean Arterial Pressure (MAP), of length T minutes prior to $t_0$ is modeled as a T-long feature vector (called the original time series OTS). These vectors are used for training (using 70% data, with 5 fold cross validation) and testing (using 30% data) an SVM model for classifying them as AHE or not. In effect, we try to classify sensor data prior to AHE event as a predictor for ensuing AHE condition. Since C group data did not have a time marker $t_0$ we selected a random but continuous time series of length T from each of the C group patients. The offset time window length T is varied as 30, 60, 90, 120, 150, and 180 minutes as an expanding time window. In the next step, the raw feature vectors are quantized using severity quantizer to form a quantized time series (QTS). The quantization levels (denoted by L) are varied as 5, 10, 15, and 20. For instance, when L=10, the each of the OTS MAP values between 60 mmHg and 50 mmHg are quantized into the same severity symbol, say "A–", whereas for L=5, the symbol "A–" quantizes all OTS MAP values between 60 mmHg and 55 mmHg. In the third step, the QTS are summarized and motifs extracted to form RASPRO Motif Time Series (MTS), with varying observation time window sizes W: 5, 10 and 15 minutes. The W corresponds to the time window in which all the severity symbols in the QTS is converted to a single consensus symbol. The QTS and MTS are then given as input to train and test the SVM model (one for QTS and another for MTS) for predicting AHE. A comparison of OTS, QTS, and MTS is done using the statistical measure of binary classification, the F-score. An F-score (also called F1 score) is calculated as:

$$F_1 \text{score} = \frac{2 * \text{Precision} * \text{Recall}}{\text{Precision} + \text{Recall}} \quad (14)$$

Figure 8A:
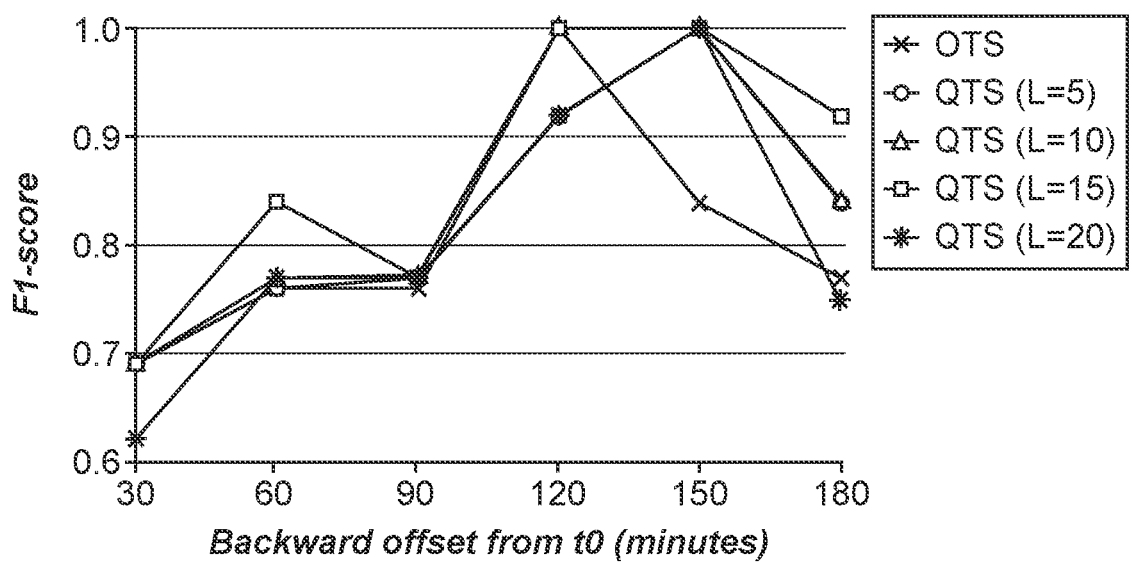
FIG. 8A shows the comparison of F1-score of OTS and QTS for classification of AHE using expanding time windows shows better performance of QTS with L=15.

From the comparative analysis of OTS and QTS as shown in FIG. 8A, we observe that QTS with L=15 has better F1-score in comparison to OTS in all the time-offsets T, although the root mean square error (RMSE) between these two series is an insignificant 0.001, pointing to the fact that OTS could be replaced with QTS. We select this QTS (L=15) and then compare it with MTS of varying time windows in FIG. 8B.

Figure 8B:
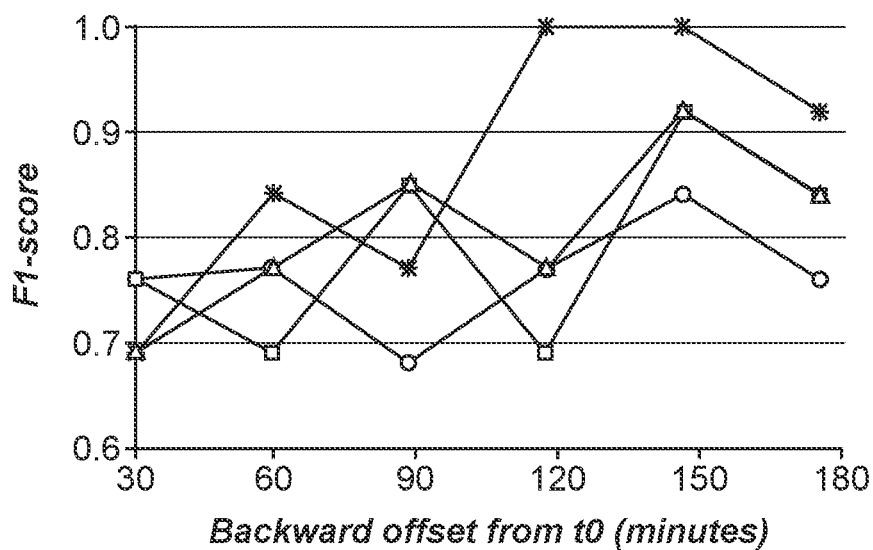
FIG. 8B shows the comparison of F1-score of QTS (L=15) and MTS (varying W) for classification of AHE using expanding time windows.
Figure 8C:
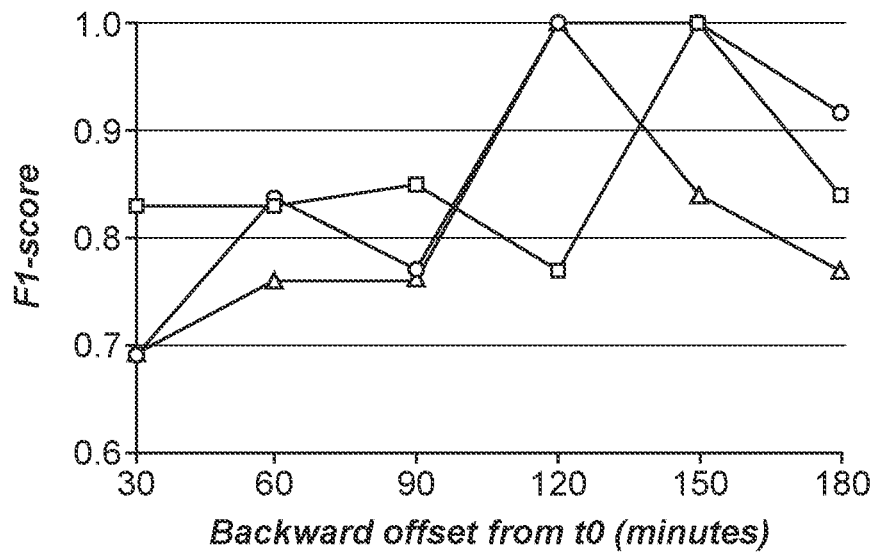
FIG. 8C shows the comparison of F1-score of OTS with QTSmax and MTSmax corresponding to best performing L and W values respectively for classifying AHE using expanding time windows.
Figure 8D:
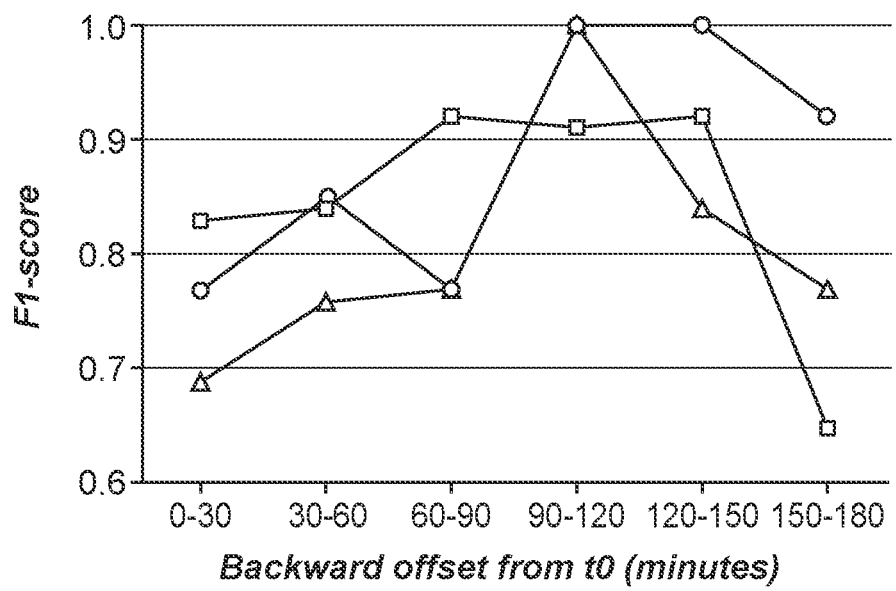
FIG. 8D shows the comparison of F1-score of OTS with QTSmax and MTSmax corresponding to best performing L and W values respectively for classifying AHE using moving window of 30 minutes duration.

We observe from FIG. 8B that QTS has higher F1-score compared to the best MTS with W=10. However, RMSE between QTS and MTS (W=10 and W=15) is a statistically insignificant value of 0.01, which implies that MTS using W=10 and 15 performs as good as QTS on an average across different time windows. Now, we further compare the OTS against the best performing L and W values corresponding to QTS and MTS respectively, and the results are plotted in FIG. 8C. These data points are marked as QTSmax and MTSmax respectively. In FIG. 8D, QTSmax and MTSmax show closely similar F1-score with the RMSE as 0.018. Going further, we used data from a moving window of 30 minutes each, instead of an expanding window. The comparative analysis of OTS against the best L and W values corresponding to QTS and MTS plotted in FIG. 8D show that MTS and QTS perform better than OTS in most of the time intervals, while the RMSE between MTS and QTS is 0.018 on an average. From these results, we can conclude that quantized symbols, as well as summarized motifs, are better in many cases and at least as good as raw time series in classifying the predictor data as AHE or not both in expanding and moving windows.

Evaluating Prediction Hypothesis: The next task is to find out if QTS and MTS can also be used as a priori data points for predicting future sensor values, which can further be used for generating critical alerts to warn the doctors ahead of time. For evaluating this, we use a data forecasting technique called ARIMA (autoregressive integrated moving average). This technique has been widely studied and used in time series prediction. In this technique we build a patient-specific ARIMA model by training it on 180 minutes of MAP data, and then use that model to predict the following 60 minutes of MAP values. The predicted and actual values are compared using the statistical measure of RMSE. First, we use OTS data for training and prediction. In the second experiment, the QTS data points are used for training, followed by the prediction of future raw time series data. These predicted raw time series values are compared with the corresponding actual OTS. Similarly, we repeat the same steps with MTS too.

Figure 9A:
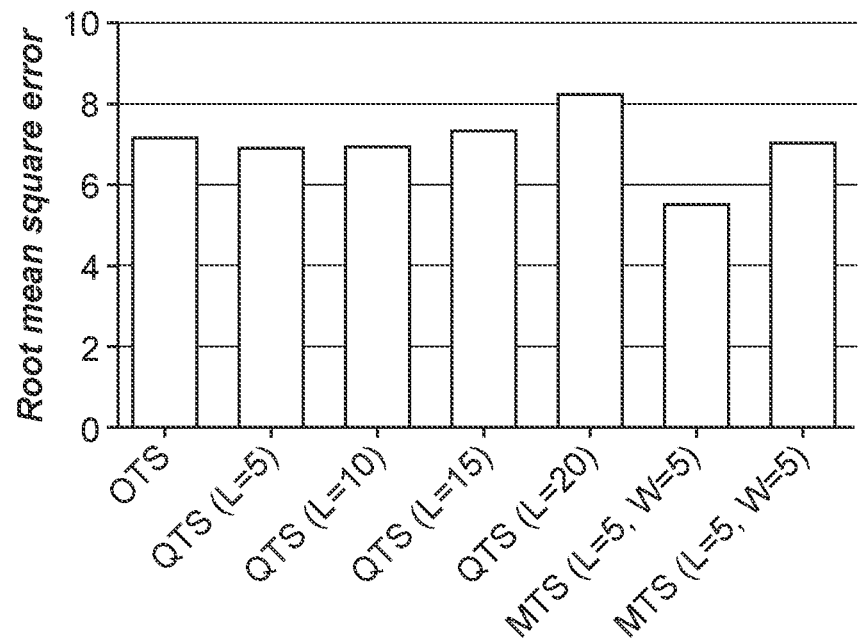
FIG. 9A shows the root mean square error for MAP prediction among group H patients using ARIMA model while using OTS, QTS (L=5, 10, 15, and 20) and MTS (L=5, and 10, while keeping W=5).
Figure 9B:
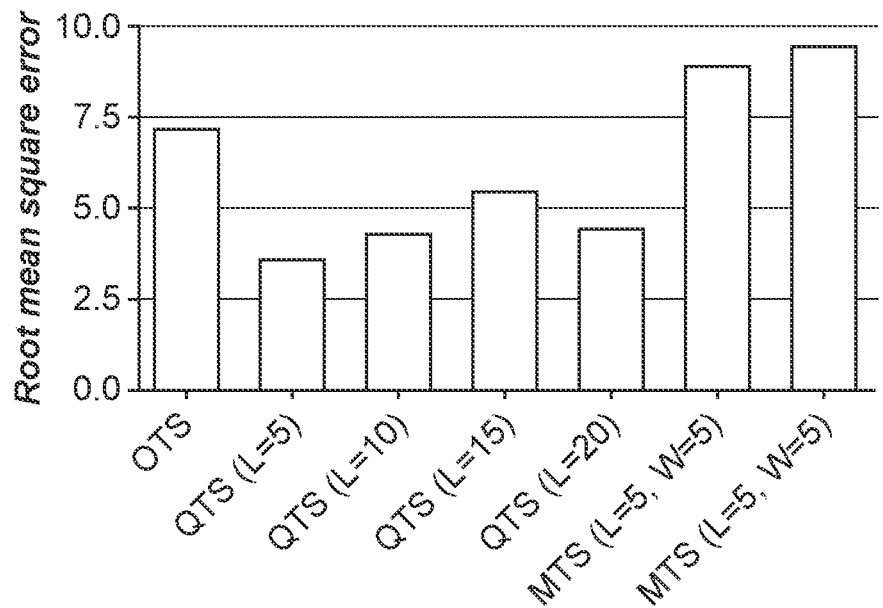
FIG. 9B illustrates the root mean square error for MAP prediction using ARIMA model for the control group patients while using OTS, QTS (L=5, 10, 15, and 20) and MTS (L=5, and 10, while keeping W=5).

FIG. 9A and FIG. 9B show the RMSE values while using OTS, QTS (with L=5, 10, 15, and 20) and MTS (with L=5, and 10, while using W=5) for H and C groups of patients. While using MTS, we had to restrict to using only a single window size of 5 since there were not enough consensus symbols for training the ARIMA model when the window size was increased to 10 and 15. FIG. 9A shows that among H group patients, the ARIMA models built using OTS, QTS, and MTS have very similar RMSE, while the least RMSE is observed when using MTS with L=5, and W=5. Among the C group patients as shown in FIG. 9A, the OTS and QTS show very similar RMSE, while MTS have at least 4 points higher RMSE in comparison. In this, the least RMSE is observed while using QTS with L=5. From these observations, we can conclude with certainty that RASPRO motifs and quantized severity symbols can be used for predicting future sensor values, even up to 60 minutes using a patient specific trained ARIMA model, thereby proving our prediction hypothesis.

Evaluating Personalization Hypothesis: The third hypothesis aims to find out if there are patient specific custom severity levels, and summarization frequencies, which if optimized could lead to better accuracies in diagnosis. For this, we further analyze our earlier results. We observe from FIG. 8C and FIG. 8D that by selecting different severity quantization levels (L) and through varying the summarization window size (W), we are able to predict the onset of AHE with higher F1-score. This supports an argument for using disease and time-specific L and W values for achieving better accuracy in classification problems. Furthermore, we see from ARIMA prediction results as shown in FIG. 9A and FIG. 9B that by using different L and W values among different groups of patients (or population) we can achieve better prediction accuracy. Hence, among high-risk patients, we can use MTS (L=5, W=5) configuration, while among other patients we can use QTS of (L=5 or 20) for best results. These results further support our third hypothesis, that there exists an opportunity for personalization at least at a sub-group or population level.

Though the above experiments using AHE are only representative of how step-wise precision, personalization, and prevention can be achieved using RASPRO, the practitioners as a whole agree that in wide-ranging scenarios patient-sensor-disease-time specific severity levels need to be defined that is both practical to manage alerts as well as effective in identifying emergencies Although the detailed description contains many specifics, these should not be construed as limiting the scope of the invention but merely as illustrating different examples and aspects of the invention. While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

What is claimed is:

1. A method for remote monitoring of a patient, comprising:
   a. obtaining a sensor data from one or more sensors attached to the patient's body;
   b. transmitting the sensor data to a first mobile computing device, wherein the sensor data is transmitted to the mobile computing device through a wired or a short range wireless communication network;
   c. transmitting the sensor data to a processing, analytics and storage (PAS) unit, wherein the first mobile computing device transmits the data to the PAS unit through a wireless communication network;
   d. detecting one or more abnormalities in the sensor data, wherein said one or more abnormalities is determined by periodic assessment of the sensor data in the first mobile computing device, the PAS unit or a combination thereof;
   e. determining a quantized severity for the one or more abnormalities in the PAS unit, wherein said determining comprise converting raw sensor values to a series of clinically relevant severity symbols arranged in a patient specific matrix (PSM);
   f. identifying the one or more abnormality to exceed a personalized severity threshold over the assessment period by a machine learning model, wherein the severity threshold for the patient is determined from sensor data, inter-sensor correlation, patient's historical data, doctor's inputs, inter-patient machine learning models obtained from hospital information system (HIS), or a combination thereof;
   g. generating an alert measure index based on the personalized severity threshold;
   h. sending a notification of the one or more abnormality to the first mobile computing device; and
   i. sending a notification of the one or more abnormality to a second mobile computing device, wherein the second mobile computing device is connected to a Health Service Provider (HSP), said notification includes an estimate of time available to the HSP for effective intervention, and wherein medium of notification to the first and second mobile computing device is determined based on at least data criticality.

2. The method of claim 1, wherein said obtaining a sensor data from one or more sensors attached to the patient's body comprise obtaining a blood pressure level, a blood glucose level, an oxygen saturation (SpO2) level, an electrocardiogram (ECG) data, motion detection system data, accelerometer data, GPRS data, or a combination thereof.

3. The method of claim 1, wherein said detecting the one or more abnormality in sensor data is indicative of a cardiovascular disease in the patient.

4. The method of claim 1, wherein said transmitting the sensor data to the first mobile computing device comprise transmitting over a GSM, 2G, 3G, 4G, LTE, Wi-Fi network or an ad-hoc network created with neighboring wireless terminals.

5. The method of claim 1, further comprising transmitting the sensor data to one or more mobile computing device connected to other patients or HSP over a wireless network.

6. The method of claim 1, wherein said transmitting the sensor data to a processing, analytics and storage (PAS) unit comprise transmitting to a local PAS unit, a remote PAS unit, a hospital PAS unit comprising a hospital information system (HIS), or a combination thereof.

7. The method of claim 1, wherein said sending a notification of the abnormality to a second mobile computing device comprise presenting patient health status to health service provider based on the criticality of data.

8. The method of claim 1, further comprising analyzing the sensor data by visualization, monitoring, analysis or intervention tools by the health service provider.

9. The method of claim 1, further comprising directing a doctor, hospital, caregiver, or emergency responder to attend to the patient.

10. The method of claim 1, wherein the medium of notification is further determined based on patient profile, available communication media, power availability of the mobile computing devices and sensors, location of the at least one processing, analytics and storage (PAS) unit, or a combination thereof.

11. The method of claim 1, further comprising sending a request from the second mobile computing device to the first mobile computing device, wherein the request is configured to pull data from the first mobile computing device, the PAS unit, or a combination thereof in an increasing level of data precision, wherein the data comprises alerts, quantized severity levels, frequency maps of severity exceeding the severity threshold, sensor data, raw sensor values, or any combination thereof.

12. The method of claim 11, wherein the request is initiated by sending an SMS from the second mobile device to the first mobile device.

13. The method of claim 1, wherein said severity is determined through a severity quantization technique that converts multi-sensor values to severity symbols based on a combination of sensor values, inter-sensor correlation, patient's historical data, doctors' inputs, and inter-patient machine learning model.

14. The method of claim 1, wherein the severity quantizer is adjusted such that the various sensor values are interpreted differently according to the diagnostic interest of one or more doctors.

15. The method of claim 1, wherein the method includes defining the routing and power policies based on reliable delivery of relevant health data to the HSPs.

16. The method of claim 1, further comprising:
classifying the data as routine or critical data;
sending the critical data via a higher priority channel such as a direct link or a cellular GSM; and
sending routine data using any available channel.

17. The method of claim 1, wherein the communication is prioritized in the PAS unit based on a combination of user location using GPS or other localization techniques, power availability in the mobility of data via smartphone and sensors, and health criticality of the patient.

18. A system for use in remote monitoring of a patient, comprising:
a. at least one sensor attached to the patient's body to obtain sensor data;
b. a data aggregation and transmission unit, wherein the data aggregation and transmission unit is interfaced with the at least one sensor to receive the sensor data;
c. a first mobile computing device, wherein the first mobile computing device is configured to receive and transmit the sensor data through a wireless communication network;
d. at least one processing, analytics and storage (PAS) unit, wherein the PAS unit is configured to receive the sensor data from the first mobile computing device, wherein the first mobile computing device, the PAS unit, or a combination thereof is configured to detect one or more abnormality in the sensor data over an assessment period, quantize a severity by converting raw sensor values to a series of clinically relevant severity symbols arranged in a patient specific matrix (PSM), identify if quantized severity exceeds a personalized severity threshold over the assessment period for the patient by a machine learning model based on sensor data, inter-sensor correlation, patient's historical data, doctor's inputs, inter-patient machine learning models obtained from hospital information system (HIS), or a combination thereof, and generate an alert measure index based on the personalized severity threshold; and
e. a second mobile computing device, wherein the second mobile computing device is connected to a Health Service Provider (HSP), wherein the system is configured to notify the first and the second mobile computing devices when the quantized severity exceeds the severity threshold and includes an estimate of time available to the HSP for effective intervention and wherein medium of notification to the first and second mobile computing device is determined based on at least data criticality.

19. The system of claim 18, wherein the at least one sensor is a BP sensor, a glucose sensor, a SpO2 sensor, an ECG sensor, a motion detection system, an accelerometer, a GPRS, or a combination thereof.

20. The system of claim 18, wherein the first mobile computing device, the second mobile computing device, or both is a smartphone, handheld, tablet, laptop, or a wearable device.

21. The system of claim 18, wherein the first mobile computing device is configured to transmit the sensor data through a GSM, 2G, 3G, 4G, LTE, Wi-Fi network or an Ad-hoc network created with neighboring wireless terminals.

22. The system of claim 18, wherein the at least one PAS unit comprises a local server, a remote server or a hospital server connected by a wireless network.

23. The system of claim 22, wherein the hospital server comprises a hospital information management system (HIM).

24. The system of claim 18, wherein the PAS unit includes an Application Layer with various visualization, monitoring, analysis and intervention tools.

25. The system of claim 18, wherein the medium of notification is further determined based on patient profile, available communication media, power availability of the mobile computing devices and sensors, location of the at least one processing, analytics and storage (PAS) unit, or a combination thereof.

26. A computer program product having non-volatile memory therein, carrying computer executable instructions stored thereon for remote monitoring of a patient, the instructions comprising:
   a. obtaining a sensor data from one or more sensors attached to the patient's body;
   b. transmitting the sensor data to a first mobile computing device, wherein the sensor data is transmitted to the mobile computing device through a wired or a short range wireless communication network;
   c. transmitting the sensor data to a processing, analytics and storage (PAS) unit, wherein the first mobile computing device transmits the data to the PAS unit through a wireless communication network;
   d. detecting one or more abnormalities in the sensor data, wherein said one or more abnormalities is determined by periodic assessment of the sensor data in the first mobile computing device, the PAS unit or a combination thereof;
   e. determining a quantized severity for the one or more abnormalities in the PAS unit, wherein said determining comprise converting raw sensor values to a series of clinically relevant severity symbols arranged in a patient specific matrix (PSM);
   f. identifying the one or more abnormality to exceed a personalized severity threshold over the assessment period by a machine learning model, wherein the severity threshold for the patient is determined from sensor data, inter-sensor correlation, patient's historical data, doctor's inputs, inter-patient machine learning models obtained from hospital information system (HIS), or a combination thereof;
   g. generating an alert measure index based on the personalized severity threshold;
   h. sending a notification of the one or more abnormality to the first mobile computing device; and
   i. sending a notification of the one or more abnormality to a second mobile computing device, wherein the second mobile computing device is connected to a Health Service Provider (HSP) and said notification includes an estimate of time available to the HSP for effective intervention and wherein medium of notification to the first and second mobile computing device is determined based on at least data criticality.

* * * * *